US007867274B2

(12) United States Patent
Hill et al.

(10) Patent No.: US 7,867,274 B2
(45) Date of Patent: Jan. 11, 2011

(54) VALVE APPARATUS, SYSTEM AND METHOD

(75) Inventors: Jason P. Hill, Cottage Grove, MN (US); Susan M. Shoemaker, Elk River, MN (US); William J. Drasler, Minnetonka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1196 days.

(21) Appl. No.: 11/063,681

(22) Filed: Feb. 23, 2005

(65) Prior Publication Data

US 2006/0190074 A1 Aug. 24, 2006

(51) Int. Cl.
A61F 2/06 (2006.01)
A61F 2/24 (2006.01)

(52) U.S. Cl. .................. 623/1.24; 623/1.26; 623/2.1; 623/2.12

(58) Field of Classification Search ....... 623/1.23–1.26, 623/2.17, 2.16
See application file for complete search history.

(56) References Cited

U.S. PATENT DOCUMENTS

| | | | |
|---|---|---|---|
| 3,671,979 A | 6/1972 | Moulopoulos | 3/1 |
| 4,291,420 A | 9/1981 | Reul | 3/1.5 |
| 4,787,901 A | 11/1988 | Baykut | 623/2 |
| 4,872,874 A | 10/1989 | Taheri | 623/1 |
| 4,935,030 A | 6/1990 | Alonso | 623/2 |
| 4,994,077 A | 2/1991 | Dobben | 623/2 |
| 5,002,567 A | 3/1991 | Bona et al. | 623/2 |
| 5,141,491 A | 8/1992 | Bowald | 604/22 |
| 5,163,953 A | 11/1992 | Vince | 623/2 |
| 5,219,355 A | 6/1993 | Parodi et al. | 606/191 |
| 5,254,127 A | 10/1993 | Wholey et al. | 606/153 |
| 5,327,774 A | 7/1994 | Nguyen et al. | 73/37 |
| 5,332,402 A | 7/1994 | Teitelbaum | 623/2 |
| 5,370,685 A | 12/1994 | Stevens | 623/2 |
| 5,411,552 A | 5/1995 | Anderson et al. | 623/2 |
| 5,469,868 A | 11/1995 | Reger | 128/898 |
| 5,480,423 A | 1/1996 | Ravenscroft et al. | 623/1 |
| 5,500,014 A | 3/1996 | Quijano et al. | 623/2 |
| 5,545,214 A | 8/1996 | Stevens | 623/2 |
| 5,554,185 A | 9/1996 | Block et al. | 623/2 |
| 5,643,208 A | 7/1997 | Parodi | 604/96 |
| 5,693,087 A | 12/1997 | Parodi | 623/1 |
| 5,713,953 A | 2/1998 | Vallana et al. | 623/2 |
| 5,716,370 A | 2/1998 | Williamson, IV et al. | 606/153 |

(Continued)

FOREIGN PATENT DOCUMENTS

EP 0 380 666 8/1990

(Continued)

OTHER PUBLICATIONS

European Office Action in related European Patent Application No. EP 06734605.6. May 31, 2010. 5 pgs.

(Continued)

*Primary Examiner*—William H Matthews
*Assistant Examiner*—Jason-Dennis Stewart
(74) *Attorney, Agent, or Firm*—Brooks, Cameron & Huebsch, PLLC

(57) ABSTRACT

A venous valve with a frame and a cover on the frame for unidirectional flow of a liquid through the valve.

10 Claims, 10 Drawing Sheets

U.S. PATENT DOCUMENTS

| | | | | |
|---|---|---|---|---|
| 5,735,859 | A | 4/1998 | Fischell et al. | 606/108 |
| 5,741,326 | A | 4/1998 | Solovay | 623/1 |
| 5,741,333 | A | 4/1998 | Frid | 623/12 |
| 5,800,506 | A | 9/1998 | Perouse | 623/1 |
| 5,824,061 | A | 10/1998 | Quijano et al. | 623/2 |
| 5,879,320 | A | 3/1999 | Cazenave | 604/8 |
| 5,895,419 | A | 4/1999 | Tweden et al. | 623/2 |
| 5,910,170 | A | 6/1999 | Reimink et al. | 623/2 |
| 6,010,531 | A | 1/2000 | Donlon et al. | 623/2 |
| 6,042,607 | A | 3/2000 | Williamson, IV et al. | 623/2 |
| 6,139,575 | A | 10/2000 | Shu et al. | 623/2.12 |
| 6,287,334 | B1 | 9/2001 | Moll et al. | 623/1.24 |
| 6,312,447 | B1 | 11/2001 | Grimes | 606/219 |
| 6,355,030 | B1 | 3/2002 | Aldrich et al. | 606/28 |
| 6,402,780 | B2 | 6/2002 | Williamson, IV et al. | 623/2.11 |
| 6,419,696 | B1 | 7/2002 | Ortiz et al. | 623/2.37 |
| 6,425,916 | B1 | 7/2002 | Garrison et al. | 623/2.11 |
| 6,440,164 | B1 | 8/2002 | DiMatteo et al. | 623/1.24 |
| 6,451,054 | B1 | 9/2002 | Stevens | 623/2.11 |
| 6,454,799 | B1 | 9/2002 | Schreck | 623/2.18 |
| 6,461,366 | B1 | 10/2002 | Seguin | 606/144 |
| 6,503,272 | B2 | 1/2003 | Duerig et al. | 623/1.24 |
| 6,508,833 | B2 | 1/2003 | Pavcnik et al. | 623/1.15 |
| 6,564,805 | B2 | 5/2003 | Garrison et al. | 128/898 |
| 6,569,196 | B1 | 5/2003 | Vesely | 623/2.14 |
| 6,602,286 | B1 | 8/2003 | Strecker | 623/1.24 |
| 6,629,534 | B1 | 10/2003 | St. Goar et al. | 128/898 |
| 6,635,085 | B1 | 10/2003 | Caffey et al. | 623/2.1 |
| 6,666,885 | B2 | 12/2003 | Moe | 623/2.12 |
| 6,666,886 | B1 | 12/2003 | Tranquillo et al. | 623/2.42 |
| 6,669,725 | B2 | 12/2003 | Scott | 623/2.36 |
| 6,673,109 | B2 | 1/2004 | Cox | 623/2.12 |
| 6,676,698 | B2 | 1/2004 | McGuckin, Jr. et al. | 623/1.24 |
| 6,676,702 | B2 | 1/2004 | Mathis | 623/2.36 |
| 6,682,558 | B2 | 1/2004 | Tu et al. | 623/2.11 |
| 6,682,559 | B2 | 1/2004 | Myers et al. | 623/2.13 |
| 6,685,739 | B2 | 2/2004 | DiMatteo et al. | 623/1.24 |
| 6,692,512 | B2 | 2/2004 | Jang | 606/200 |
| 6,695,866 | B1 | 2/2004 | Kuehn et al. | 606/213 |
| 6,695,878 | B2 | 2/2004 | McGuckin, Jr. et al. | 623/1.19 |
| 6,709,456 | B2 | 3/2004 | Langberg et al. | 623/2.37 |
| 6,709,457 | B1 | 3/2004 | Otte et al. | 623/2.4 |
| 6,716,241 | B2 | 4/2004 | Wilder et al. | 623/1.24 |
| 6,716,244 | B2 | 4/2004 | Klaco | 623/2.4 |
| 6,719,767 | B1 | 4/2004 | Kimblad | 606/151 |
| 6,719,784 | B2 | 4/2004 | Henderson | 623/1.44 |
| 6,719,786 | B2 | 4/2004 | Ryan et al. | 623/2.11 |
| 6,719,787 | B2 | 4/2004 | Cox | 623/2.12 |
| 6,719,788 | B2 | 4/2004 | Cox | 623/2.12 |
| 6,719,789 | B2 | 4/2004 | Cox | 623/2.13 |
| 6,719,790 | B2 | 4/2004 | Brendzel et al. | 623/2.4 |
| 6,723,038 | B1 | 4/2004 | Schroeder et al. | 600/16 |
| 6,723,122 | B2 | 4/2004 | Yang et al. | 623/2.1 |
| 6,723,123 | B1 | 4/2004 | Kazatchkov et al. | 623/2.2 |
| 6,726,715 | B2 | 4/2004 | Sutherland | 623/2.1 |
| 6,726,716 | B2 | 4/2004 | Marquez | 623/2.36 |
| 6,726,717 | B2 | 4/2004 | Alfieri et al. | 623/2.36 |
| 6,730,118 | B2 | 5/2004 | Spenser et al. | 623/1.24 |
| 6,730,121 | B2 | 5/2004 | Ortiz et al. | 623/2.17 |
| 6,730,122 | B1 | 5/2004 | Pan et al. | 623/2.33 |
| 6,736,845 | B2 | 5/2004 | Marquez et al. | 623/2.11 |
| 6,736,846 | B2 | 5/2004 | Cox | 623/2.12 |
| 6,749,630 | B2 | 6/2004 | McCarthy et al. | 623/2.36 |
| 6,752,813 | B2 | 6/2004 | Goldfarb et al. | 606/139 |
| 6,752,828 | B2 | 6/2004 | Thornton | 623/1.24 |
| 6,755,857 | B2 | 6/2004 | Peterson et al. | 623/2.17 |
| 6,761,734 | B2 | 7/2004 | Suhr | 623/1.35 |
| 6,761,735 | B2 | 7/2004 | Eberhardt et al. | 623/2.1 |
| 6,764,494 | B2 | 7/2004 | Menz et al. | 606/159 |
| 6,764,508 | B1 | 7/2004 | Roehe et al. | 623/2.11 |
| 6,764,509 | B2 | 7/2004 | Chinn et al. | 623/2.12 |
| 6,764,510 | B2 | 7/2004 | Vidlund et al. | 623/2.34 |
| 6,767,362 | B2 | 7/2004 | Schreck | 623/2.11 |
| 6,769,434 | B2 | 8/2004 | Liddicoat et al. | 128/898 |
| 6,770,083 | B2 | 8/2004 | Seguin | 606/142 |
| 6,780,200 | B2 | 8/2004 | Jansen | 623/2.17 |
| 6,786,924 | B2 | 9/2004 | Ryan et al. | 623/2.36 |
| 6,786,925 | B1 | 9/2004 | Schoon et al. | 623/2.38 |
| 6,790,229 | B1 | 9/2004 | Berreklouw | 623/2.1 |
| 6,790,230 | B2 | 9/2004 | Beyersdorf et al. | 623/2.18 |
| 6,790,231 | B2 | 9/2004 | Liddicoat et al. | 623/2.37 |
| 6,793,673 | B2 | 9/2004 | Kowalsky et al. | 623/2.36 |
| 6,797,000 | B2 | 9/2004 | Simpson et al. | 623/2.15 |
| 6,797,001 | B2 | 9/2004 | Mathis et al. | 623/2.37 |
| 6,797,002 | B2 | 9/2004 | Spence et al. | 623/2.38 |
| 6,802,860 | B2 | 10/2004 | Cosgrove et al. | 623/2.11 |
| 6,805,710 | B2 | 10/2004 | Bolling et al. | 623/2.36 |
| 6,805,711 | B2 | 10/2004 | Quijano et al. | 623/2.37 |
| 6,810,882 | B2 | 11/2004 | Langberg et al. | 128/898 |
| 6,821,297 | B2 | 11/2004 | Snyders | 623/2.18 |
| 6,824,562 | B2 | 11/2004 | Mathis et al. | 623/2.36 |
| 6,830,584 | B1 | 12/2004 | Seguin | 623/2.11 |
| 6,830,585 | B1 | 12/2004 | Artof et al. | 623/2.11 |
| 6,837,902 | B2 | 1/2005 | Nguyen et al. | 623/2.13 |
| 6,840,246 | B2 | 1/2005 | Downing | 128/898 |
| 6,840,957 | B2 | 1/2005 | DiMatteo et al. | 623/1.24 |
| 6,846,324 | B2 | 1/2005 | Stobie | 623/2.11 |
| 6,846,325 | B2 | 1/2005 | Liddicoat | 623/2.4 |
| 6,858,039 | B2 | 2/2005 | McCarthy | 623/2.36 |
| 6,869,444 | B2 | 3/2005 | Gabbay | 623/2.36 |
| 6,908,481 | B2 | 6/2005 | Cribier | 623/2.11 |
| 6,945,996 | B2 | 9/2005 | Sedransk | 623/2.12 |
| 6,951,571 | B1 | 10/2005 | Srivastava | 623/1.24 |
| 6,951,573 | B1 | 10/2005 | Dilling | 623/2.2 |
| 6,953,332 | B1 | 10/2005 | Kurk et al. | 425/275 |
| 6,955,689 | B2 | 10/2005 | Ryan et al. | 623/2.36 |
| 6,958,076 | B2 | 10/2005 | Acosta et al. | 623/1.24 |
| 6,962,605 | B2 | 11/2005 | Cosgrove et al. | 623/2.36 |
| 6,964,682 | B2 | 11/2005 | Nguyen-Thien-Nhon et al. | 623/2.11 |
| 6,964,683 | B2 | 11/2005 | Kowalsky et al. | 623/2.36 |
| 6,964,684 | B2 | 11/2005 | Ortiz et al. | 623/2.37 |
| 6,966,925 | B2 | 11/2005 | Stobie | 623/2.11 |
| 6,966,926 | B2 | 11/2005 | Mathis | 623/2.36 |
| 6,974,464 | B2 | 12/2005 | Quijano et al. | 606/108 |
| 6,974,474 | B2 | 12/2005 | Pavcnik et al. | 623/1.24 |
| 6,974,476 | B2 | 12/2005 | McGuckin, Jr. et al. | 623/2.36 |
| 6,976,995 | B2 | 12/2005 | Mathis et al. | 623/2.37 |
| 6,979,350 | B2 | 12/2005 | Moll et al. | 623/1.24 |
| 6,986,775 | B2 | 1/2006 | Morales et al. | 606/139 |
| 6,989,027 | B2 | 1/2006 | Allen et al. | 623/2.18 |
| 6,989,028 | B2 | 1/2006 | Lashinski et al. | 623/2.37 |
| 6,997,950 | B2 | 2/2006 | Chawla | 623/2.1 |
| 6,997,951 | B2 | 2/2006 | Solem et al. | 623/2.37 |
| 7,004,176 | B2 | 2/2006 | Lau | 128/898 |
| 7,007,396 | B2 | 3/2006 | Rudko et al. | 33/512 |
| 7,011,669 | B2 | 3/2006 | Kimblad | 606/151 |
| 7,011,681 | B2 | 3/2006 | Vesely | 623/2.11 |
| 7,011,682 | B2 | 3/2006 | Lahsinski et al. | 623/2.37 |
| 7,018,406 | B2 | 3/2006 | Seguin et al. | 623/2.1 |
| 7,018,407 | B1 | 3/2006 | Wright et al. | 623/2.11 |
| 7,018,408 | B2 | 3/2006 | Bailey et al. | 623/2.11 |
| 7,022,134 | B1 | 4/2006 | Quijano et al. | 623/1.24 |
| 7,025,780 | B2 | 4/2006 | Gabbay | 623/2.13 |
| 7,033,390 | B2 | 4/2006 | Johnson et al. | 623/2.11 |
| 7,037,333 | B2 | 5/2006 | Myers et al. | 623/2.13 |
| 7,037,334 | B1 | 5/2006 | Hlavka et al. | 623/2.36 |
| 7,041,128 | B2 | 5/2006 | McGuckin, Jr. et al. | 623/1.36 |
| 7,041,132 | B2 | 5/2006 | Quijano et al. | 623/2.11 |
| 7,044,966 | B2 | 5/2006 | Svanidze et al. | 623/2.1 |
| 7,044,967 | B1 | 5/2006 | Solem et al. | 623/2.36 |
| 7,048,754 | B2 | 5/2006 | Martin et al. | 606/232 |
| 7,048,757 | B2 | 5/2006 | Shaknovich | 623/1.24 |
| 7,052,487 | B2 | 5/2006 | Cohn et al. | 604/509 |

| Patent/Pub No. | Date | Inventor | Class |
|---|---|---|---|
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,070,618 B2 | 7/2006 | Streeter | 623/2.36 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 7,195,641 B2* | 3/2007 | Palmaz et al. | 623/2.18 |
| 2001/0039450 A1* | 11/2001 | Pavcnik et al. | 623/1.24 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0107565 A1* | 8/2002 | Greenhalgh | 623/1.24 |
| 2002/0123802 A1* | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Liddicoat et al. | 623/2.11 |
| 2002/0188348 A1* | 12/2002 | DiMatteo et al. | 623/1.24 |
| 2002/0198594 A1 | 12/2002 | Schreck | 623/2.11 |
| 2003/0014104 A1 | 1/2003 | Cribier | |
| 2003/0023303 A1* | 1/2003 | Palmaz et al. | 623/2.18 |
| 2003/0050694 A1 | 3/2003 | Yang et al. | 623/2.11 |
| 2003/0078652 A1* | 4/2003 | Sutherland | 623/2.12 |
| 2003/0130729 A1 | 7/2003 | Paniagua et al. | 623/2.11 |
| 2003/0153943 A1* | 8/2003 | Michael et al. | 606/200 |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/151 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |

| Publication No. | Date | Inventor | Class |
|---|---|---|---|
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0249452 A1 | 12/2004 | Adams et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0060030 A1 | 3/2005 | Lashinski et al. | 623/2.37 |
| 2005/0075728 A1 | 4/2005 | Nguyen et al. | 623/2.17 |
| 2005/0113910 A1 | 5/2005 | Paniagua et al. | 623/2.14 |
| 2005/0137685 A1 | 6/2005 | Nieminen et al. | 623/2.11 |
| 2005/0149179 A1 | 7/2005 | Mathis et al. | 623/2.11 |
| 2005/0203605 A1 | 9/2005 | Dolan | 623/1.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009804 A1 | 1/2006 | Pederson | 607/2 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Starksen et al. | 604/510 |
| 2006/0025784 A1 | 2/2006 | Starksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069429 A1 | 3/2006 | Spence et al. | 623/2.11 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |

| Publication No. | Date | Inventor | Class |
|---|---|---|---|
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161249 A1 | 7/2006 | Realyvasquez et al. | 623/2.11 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| EP | 0 466 518 | 1/1992 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |
| WO | WO 2004/082537 | 9/2004 |
| WO | WO 2004/082538 | 9/2004 |
| WO | WO 2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/103223 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |
| WO | WO 2005/000152 | 1/2005 |
| WO | WO 2005/002424 | 1/2005 |
| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |
| WO | WO 2005/018507 | 3/2005 |
| WO | WO 2005/027790 | 3/2005 |
| WO | WO 2005/046488 | 5/2005 |
| WO | WO 2005/048883 | 6/2005 |
| WO | WO 2005/070342 | 8/2005 |
| WO | WO 2005/079706 | 9/2005 |
| WO | WO 2005/087139 | 9/2005 |
| WO | WO 2006/000763 | 1/2006 |
| WO | WO 2006/000776 | 1/2006 |
| WO | WO 2006/002492 | 1/2006 |
| WO | WO 2006/004679 | 1/2006 |
| WO | WO 2006/005015 | 1/2006 |
| WO | WO 2006/009690 | 1/2006 |
| WO | WO 2006/011127 | 2/2006 |
| WO | WO 2006/012011 | 2/2006 |
| WO | WO 2006/012013 | 2/2006 |
| WO | WO 2006/012038 | 2/2006 |
| WO | WO 2006/012068 | 2/2006 |
| WO | WO 2006/012322 | 2/2006 |

| | | |
|---|---|---|
| WO | WO 2006/019498 | 2/2006 |
| WO | WO 2006/026371 | 3/2006 |
| WO | WO 2006/026377 | 3/2006 |
| WO | WO 2006/026912 | 3/2006 |
| WO | WO 2006/027499 | 3/2006 |
| WO | WO 2006/028821 | 3/2006 |
| WO | WO 2006/029062 | 3/2006 |
| WO | WO 2006/031436 | 3/2006 |
| WO | WO 2006/031469 | 3/2006 |
| WO | WO 2006/032051 | 3/2006 |
| WO | WO 2006/034245 | 3/2006 |
| WO | WO 2006/035415 | 4/2006 |
| WO | WO 2006/041505 | 4/2006 |
| WO | WO 2006/044679 | 4/2006 |
| WO | WO 2006/048664 | 5/2006 |
| WO | WO 2006/050459 | 5/2006 |
| WO | WO 2006/050460 | 5/2006 |
| WO | WO 2006/054107 | 5/2006 |
| WO | WO 2006/054930 | 5/2006 |
| WO | WO 2006/055982 | 5/2006 |
| WO | WO 2006/060546 | 6/2006 |
| WO | WO 2006/063108 | 6/2006 |
| WO | WO 2006/063181 | 6/2006 |
| WO | WO 2006/063199 | 6/2006 |
| WO | WO 2006/064490 | 6/2006 |
| WO | WO 2006/065212 | 6/2006 |
| WO | WO 2006/065930 | 6/2006 |
| WO | WO 2006/066148 | 6/2006 |
| WO | WO 2006/066150 | 6/2006 |
| WO | WO 2006/069094 | 6/2006 |
| WO | WO 2006/070372 | 7/2006 |
| WO | WO 2006/073628 | 7/2006 |
| WO | WO 2006/076890 | 7/2006 |

OTHER PUBLICATIONS

US 6,673,110, 01/2004, Alfieri et al. (withdrawn)
US 6,723,117, 04/2004, Menz et al. (withdrawn)

* cited by examiner

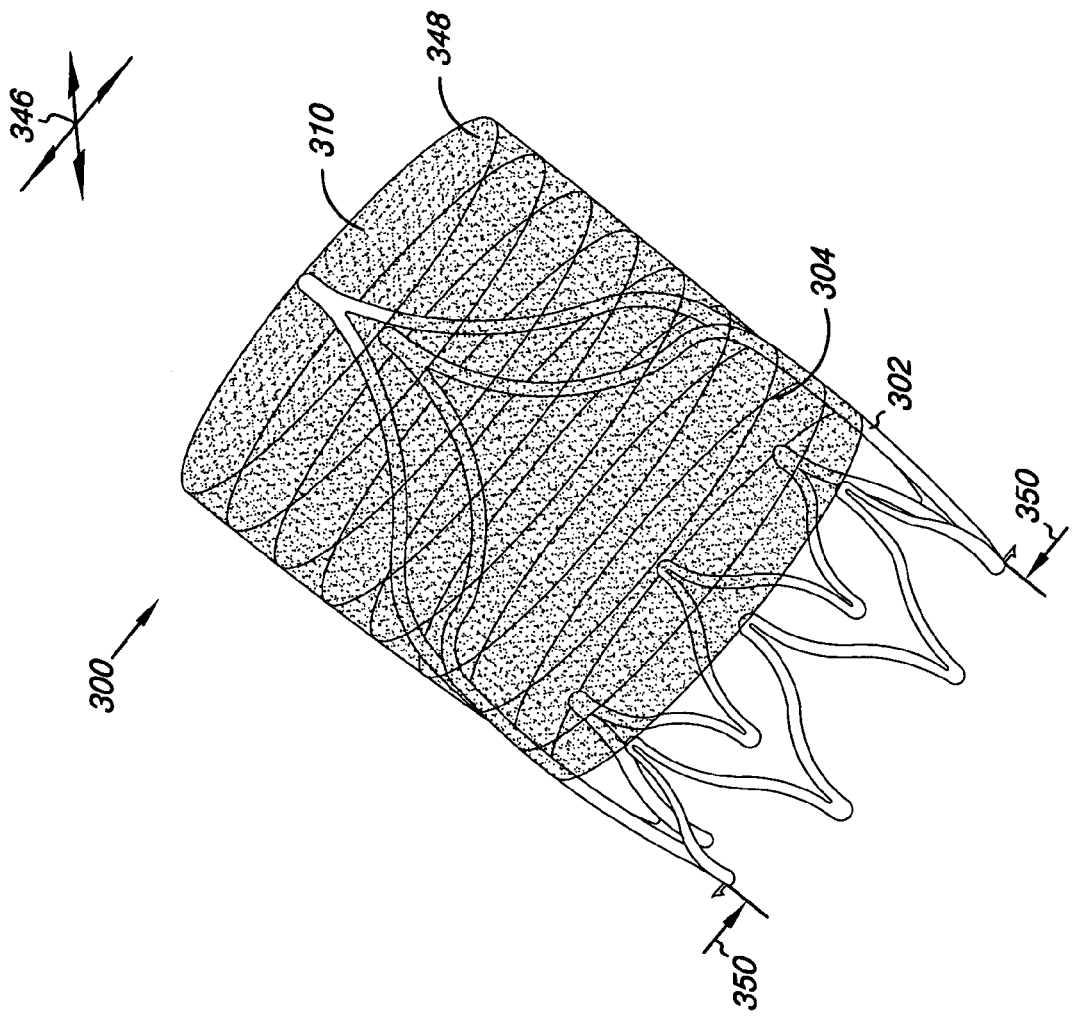
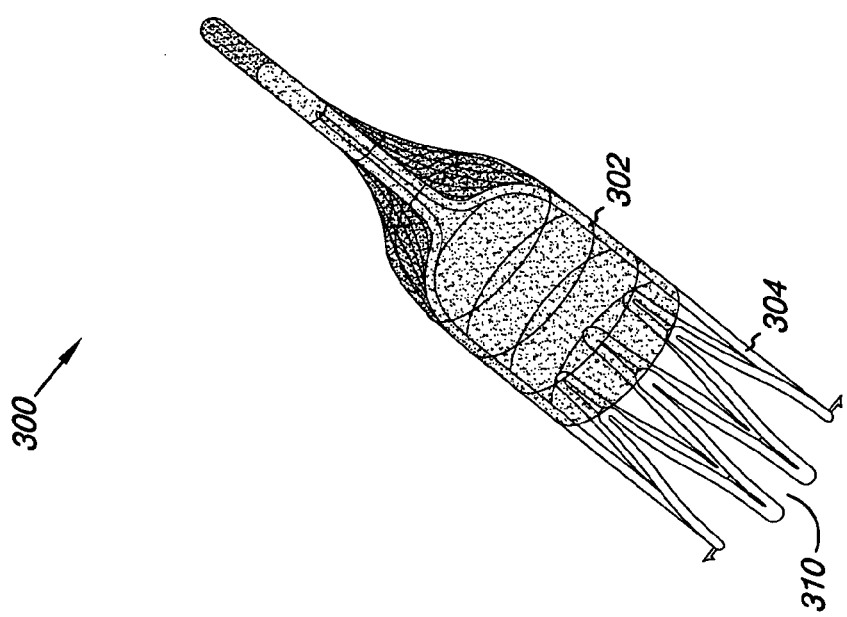
Fig. 3B
Fig. 3A

VALVE APPARATUS, SYSTEM AND METHOD

FIELD OF THE INVENTION

The present invention relates generally to apparatus, systems, and methods for use in a lumen; and more particularly to a valve apparatus, systems, and methods for use in the vasculature system.

BACKGROUND OF THE INVENTION

The venous system of the legs uses valves and muscles as part of the body's pumping mechanism to return blood to the heart. Venous valves create one way flow to prevent blood from flowing away from the heart. When valves fail, blood can pool in the lower legs resulting in swelling and ulcers of the leg. The absence of functioning venous valves can lead to chronic venous insufficiency.

Techniques for both repairing and replacing the valves exist, but are tedious and require invasive surgical procedures. Direct and indirect valvuoplasty procedures are used to repair damaged valves. Transposition and transplantation are used to replace an incompetent valve. Transposition involves moving a vein with an incompetent valve to a site with a competent valve. Transplantation replaces an incompetent valve with a harvested valve from another venous site. Prosthetic valves can be transplanted into the venous system, but current devices are not successful enough to see widespread usage.

BRIEF DESCRIPTION OF THE DRAWINGS

FIGS. 3A-3B illustrate a valve in an expanded and a collapsed state.

DETAILED DESCRIPTION

Figure 1A:
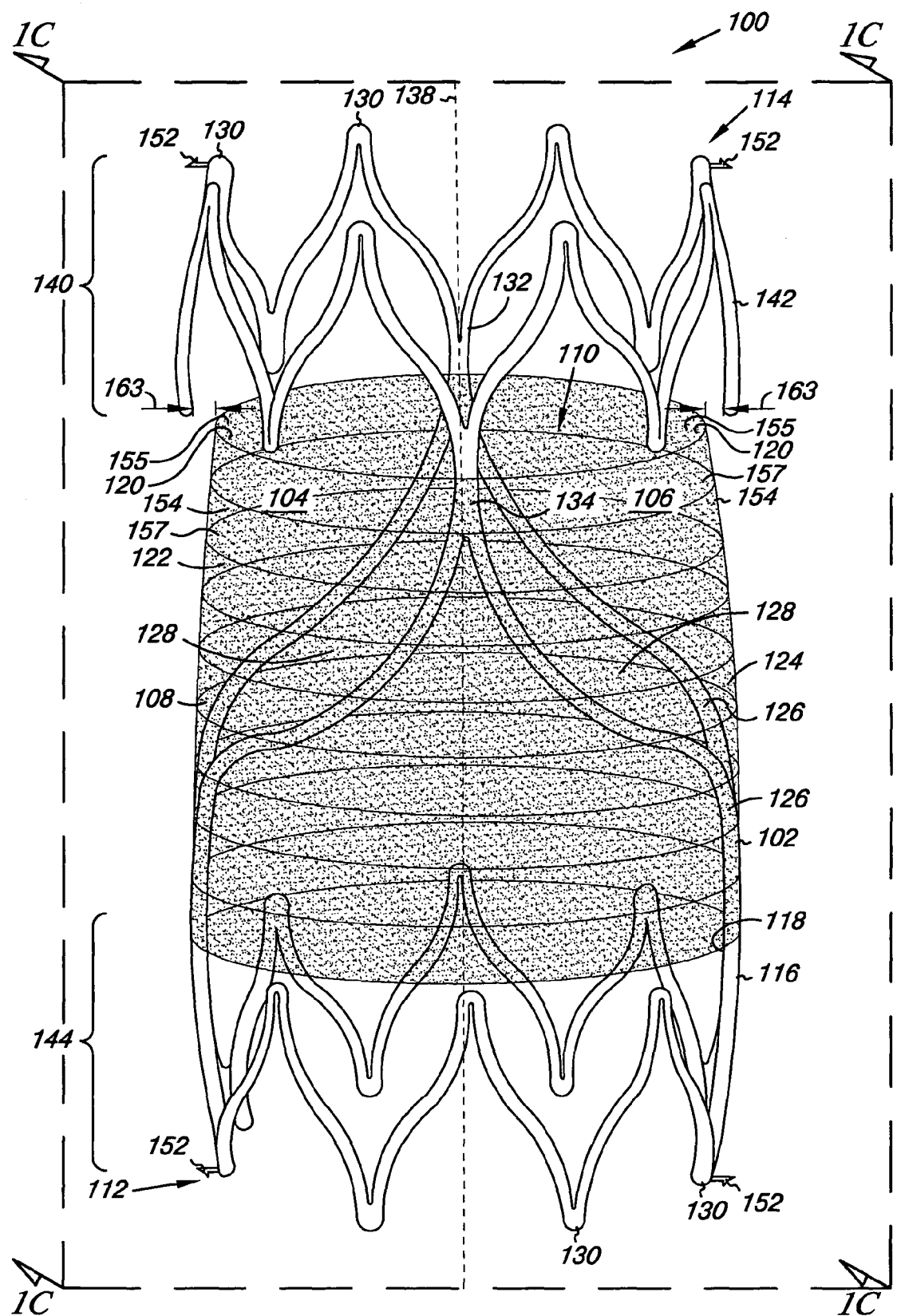
FIGS. 1A-1B illustrate an embodiment of a valve.

Embodiments of the present invention are directed to an apparatus, system, and method for valve replacement or augmentation. For example, the apparatus can include a valve that can be used to replace or augment an incompetent valve in a body lumen. Embodiments of the valve can include a frame and cover that can be implanted through minimally-invasive techniques into the body lumen. In one example, embodiments of the apparatus, system, and method for valve replacement or augmentation may help to maintain antegrade blood flow, while decreasing retrograde blood flow in a venous system of individuals having venous insufficiency, such as venous insufficiency in the legs.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Fig. can also apply to the element shown in one or more additional Figs.

FIGS. 1A-1D and 3A-3B provide illustrations of various embodiments of a valve of the present invention. Generally, the valve can be implanted within the fluid passageway of a body lumen, such as for replacement or augmentation of a valve structure within the body lumen (e.g., a venous valve). In one embodiment, the valve of the present invention may be beneficial to regulate the flow of a bodily fluid through the body lumen in a single direction.

FIGS. 1A-1D illustrate one embodiment of a venous valve 100. Venous valve 100 includes a frame 102, a first leaflet 104 and a second leaflet 106 formed from a cover 108, where the frame 102 and the leaflets 104 and 106 can resiliently radially collapse and expand, as will be discussed herein. Among other things, the frame 102 and the leaflets 104 and 106 define a lumen 110 of the valve 100. The lumen 110 allows for, among other things, fluid (e.g., blood) to move through the valve 100.

The frame 102 also includes a first end 112 and a second end 114. The first end 112 and the second end 114 define a length of the frame 102 and of the valve 100. In one embodiment, the length of valve 100 can have a number of values. As will be appreciated, the length of valve 100 can be determined based upon the location into which the valve 100 is to be implanted. In other words, the length of the valve 100 can be patient specific. Examples of values for the length include 4 millimeters to 30 millimeters.

The frame 102 further includes an outer surface 116 and an inner surface 118 opposite the outer surface 116. In one embodiment, the cover 108 can be located over at least a portion of the outer surface 116 of the frame 102. For example, the cover 108 can extend around a perimeter of the frame 102 so as to cover the outer surface 116 of the frame 102. In other words, the cover 108 can extend over the outer surface 116 of the frame 102 so as to limit, or eliminate, exposed portions of the outer surface 116 of the frame 102. In an additional embodiment, the cover 108 can be located over at least a portion of the inner surface 118 of the frame 102. A further embodiment includes the cover 108 located over at least a portion of the outer surface 116 and the inner surface 118.

The leaflets 104 and 106 further include surfaces defining a reversibly sealable opening 120 for unidirectional flow of a liquid through the lumen 110 of the valve 100. For example, the surfaces of the leaflets 104 and 106 can be deflectable between a closed configuration in which fluid flow through the lumen 110 can be restricted and an open configuration in which fluid flow through the lumen 110 can be permitted.

The cover 108 further includes a physical configuration that provides support to the shape and structure of the leaflets 104 and 106. As used herein, physical configurations that provide "support" can include structures and/or members that are integrated into and/or a part of the material that composes the cover 108 that help to maintain a pre-implant shape and size of the leaflets of the valve.

The physical configuration that provides support to the leaflets 104 and 106 can be provided in a number of ways. For example, the cover 108 can include a matrix 122 reinforced with flexible support members 124 to provide a composite structure for the leaflets 104 and 106. The flexible support members 124 can be integrated into the matrix 122 so as to help prevent deformation of the original size and shape of the leaflets 104 and 106 that may occur over time through such processes as material stretch, creep, and stress relaxation. So, for example, the integrated flexible support members 124 can be oriented to provide circumferential support to the first leaflet and the second leaflet 104 and 106.

In one embodiment, the cover 108 can have a multi-layer configuration in which at least one layer of the integrated flexible support members 124 can be integrated and/or laminated between at least one layer of the matrix 122 material. For example, as illustrated in FIGS. 1A-1D, the cover 108 includes one or more layers of the flexible support members 124 and one or more layers of the matrix 122 that contribute to enhanced mechanical and handling properties of the cover 108. As discussed herein, the layers of the flexible support members 124 can be positioned to lie in a number of different relationships to each other. For example, the layers of the flexible support members 124 can lie in coplanar relations to one another, where the layers can have a number of angular relations to one another (e.g., orthogonal relation to each other). Other configurations are also possible.

As illustrated, the leaflets 104 and 106 can also have an integrated configuration in which the flexible support members 124 are positioned within the matrix 122 material of the leaflets 104 and 106. Although the cover 108 is illustrated as having the flexible support members 124 disposed substantially in the center of a cross section of the matrix 122, it is understood that the flexible support members 124 can be disposed at a number of locations within the cover 108.

In addition, different combinations of materials (discussed herein) can be used for one or more of the flexible support members 124 and/or the matrix 122 material. For example, the flexible support members 124 of the same structure and chemistry or different structures and chemistries can be overlaid on top of one another to and combined with the matrix 122 material to fabricate a cover 108 having the desired mechanical strength and physical properties. In an additional embodiment, the cover 108 forming the leaflets 104 and 106 can have a configuration in which the matrix 122 can be formed of a first material and the flexible support members 124 can be formed of a second material different than the first material. For example, the leaflets 104 and 106 can include a top layer of the matrix 122 of the first material and a bottom layer of the matrix 122 of first material coupled to the top layer of the first material. The flexible support members 124 of the leaflets 104 and 106 can then be positioned to lie between the top and bottom layers of the first material. The matrix 122 can be integrated with the flexible support members 124 in such a way that the material of the matrix 122 penetrates through openings between the flexible support members 124 to interlock the matrix 122 and the flexible support members 124. Surfaces of adjacent layers of the matrix 122 material can also interlock with one another, regardless of whether the layers of the matrix 122 are separated by a layer of the flexible support members 124 or whether they are made from the same or different materials.

In an additional embodiment, the flexible support members 124 can include a number of forms that contribute to both the mechanical and handling properties of the cover 108. Examples of such forms for the flexible support members 124 include, but are not limited to, those selected from the group consisting of weaves, braids, meshes, knits, warped knitted (i.e., lace-like), matted, coils (continuous helically wound coils or individually positioned coils), rings, ribbons (individual or continuous), and non-woven structures including electrostatically spun fibers or fiber compositions of polymers, polymers and other materials such as various copolymers.

In addition, mechanical properties of the cover 108 can be altered by changing the density, form, and/or texture of the flexible support members 124 in one or more locations of the cover 108. Examples of suitable structures used to create the flexible support members 124 can include, for example, monofilaments, yarns, threads, braids, or bundles of fibers.

Regardless of its configuration, the composite structure of the cover 108 should possess a burst strength adequate to withstand pressures imposed by blood moving in the circulation system. In addition, the cover 108 can be sufficiently thin and pliable so as to permit radially-collapsing of the leaflets 104 and 106 portion of the valve 100 to allow the valve 100 to provide the reversibly sealable opening 120 and for delivery by catheter to a location within a body lumen. As discussed herein, different portions of the matrix 122 and/or the flexible support members 124 may be made from different materials. Adequate strength and physical properties are developed in the cover 108 through the selection of materials used to form the matrix 122 and the flexible support members 124, and the manufacturing process used to join them.

By way of example, both the matrix 122 and the flexible support members 124 can be formed of a number of materials. For example, the matrix 122 and/or the flexible support members 124 can be formed of, by way of illustration and not by limitation, thermoplastic and thermo-set polymers. Examples of these polymers include polyolefins such as polyethylene and polypropylene, polyesters such as Dacron, polyethylene terephthalate and polybutylene terephthalate, vinyl halide polymers such as polyvinyl chloride (PVC), polyvinylacetate such as ethyl vinyl acetate (EVA), polyurethanes, polymethylmethacrylate, pellethane, polyamides such as nylon 4, nylon 6, nylon 66, nylon 610, nylon 11, nylon 12 and polycaprolactam, polyaramids (e.g., KEVLAR), polystyrene-polyisobutylene-polystyrene (SIBS), segmented poly(carbonate-urethane), Rayon, fluoropolymers such as polytetrafluoroethylene (PTFE or TFE) or expanded polytetrafluoroethylene (ePTFE), ethylene-chlorofluoroethylene (ECTFE), fluorinated ethylene propylene (FEP), polychlorotrifluoroethylene (PCTFE), polyvinylfluoride (PVF), or polyvinylidenefluoride (PVDF), natural biopolymers such as cellulose, chitin, keratin, silk, and collagen, explanted veins, decellularized basement membrane materials, submucosa materials such as small intestine submucosa (SIS) or umbilical vein, or other naturally occurring extracellular matrix (ECM), and other autologous or allogeneic biological materials either treated by crosslinking or not, and mixtures and copolymers thereof. SIS and ECM materials can be autologous, allogeneic or xenograft material derived from mammals, including source, such as human, cattle, sheep, and porcine. As will be appreciated, blends or mixtures of two or more of the materials provided herein are possible. For example, SIBS can be blended with one or more basement membrane materials.

Each of the polymers noted herein may be used in conjunction with radioopaque filler materials such as barium sulfate, bismuth trioxide, bismuth carbonate, powdered tungsten, powdered tantalum, or the like so that the location of the matrix 122 and/or the flexible support members 124 may be radiographically visualized within the human body.

In another embodiment of the present invention, the polymers and blends that are used to form the composite can be used as a drug delivery matrix. To form this matrix, the polymer can be mixed with a therapeutic agent or the agent can be applied to the surface or otherwise delivered from the material. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anti-inflammatory agents; hormones such as steroids; and naturally derived or genetically engineered proteins, polysaccharides, glycoproteins, or lipoproteins, anti-thrombotic agents, anti Pt agents, anti-immunogenic agents, anti-mitotic agents, anti proliferative agents, and angiogenic agents. Matrix formulations may be formulated by mixing one or more therapeutic agents with the polymer. The therapeutic agent may be present as a liquid, a finely divided solid, or any other appropriate physical form. Typically, but optionally, the matrix will include one or more additives, such as diluents, carriers, excipients, stabilizers or the like. Additionally, radioopaque markers may be added to the composite to allow imaging of the composite after implantation.

In an additional embodiment, the flexible support members 124 can be formed of ceramics, and/or metals. Suitable ceramics for the flexible support members 124 include those formed from basalt (solidified volcanic lava), and sold under the trade identifier "Sudaglass." In one embodiment, the basalt can be mechanically crushed to provide the basalt in a fibrous form having a predetermined size of 9 to 17 microns in length. The basalt in the fibrous form can be blended with one or more of the polymers noted herein (e.g., SIBS, or polyolefins) so as to distribute the basalt in the fibrous form through the polymer matrix. In one embodiment, the basalt polymer composite can include 0.1 percent (wt.) basalt in the fibrous form. As will be appreciated, other weight percentage of basalt in the fibrous form relative polymer are possible.

The flexible support members 124 can also be formed of other nanostructures, such as carbon nanotubules. For example, carbon nano-tubules can be blended with one or more of the polymers noted herein (e.g., SIBS) so as to distribute the carbon nano-tubules through the polymer matrix. In one embodiment, the carbon nano-tubule polymer composite can include from 0.1 percent to 20 percent (wt.) carbon nano-tubules. As will be appreciated, other weight percentage of carbon nano-tubules relative polymer are possible.

The flexible support members 124 can also be formed of metals and/or metal alloys. For example, suitable metals and/or metal alloys for the flexible support members 124 include, but are not limited to, medical grade stainless steels (304, 306, 308, 316L, 318, etc.), gold, platinum, platinum alloys, palladium, rhodium, tungsten, tungsten alloys, cobalt chrome, titanium and titanium alloys, and other metal alloys such as those composed of titanium/nickel and sold under the trade identifier "Nitinol."

Heat treatment of the Nitinol alloy may also be desirable. An example of such a heat treatment includes, but is not limited to, placing the Nitinol in its desired shape onto a mandrel. The Nitinol is then heated to a temperature of 650° -750° F. for a predetermined time (e.g., two (2) to five (5) minutes), possibly (but not necessarily) annealing the constituent Nitinol. After heat treatment, the flexible support members 124 retain their shape and the Nitinol alloy retains its super-elastic properties.

The support members 124 can also include a variety of cross-sectional configurations. For example, the support members 124 can have one or more of a round (e.g., circular, oval, and/or elliptical), "ribbon" configuration with rectangular geometries with an aspect ratio of at least 0.5 (thickness/width) having perpendicular sides, one or more convex sides, or one or more concave sides; semi-circular; triangular; tubular; I-shaped; T-shaped; and trapezoidal. Theses embodiment, however, are not limited to the present examples as other cross-sectional geometries are also possible. With respect to "braid," the term can include tubular constructions in which the flexible support members 124 making up the construction are woven radially in an in-and-out fashion as they cross to form a tubular member defining a single lumen. The braid can also be constructed of flexible support members 124 of different widths. Changes in the braid can allow for pocket formation and the shape of the leaflets 104 and 106, as discussed herein. Such pocket formation can allow the valve leaflet, in one embodiment, to not assume an absolutely planar or cylindrical shape but instead form a pocket or cupped depression that is more efficient at forming a seal between the two leaflets. This rounded shape adjacent the sinus region of the valve cusp can help allow the valve cusp to be rinsed by blood as the leaflet closes.

Figure 2A:
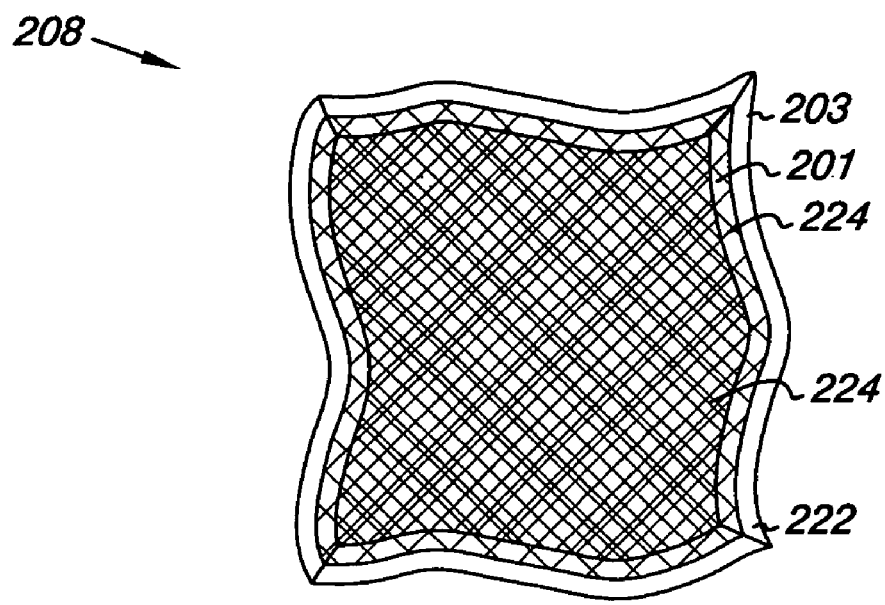
FIGS. 2A-2D illustrate segment views of embodiments of a cover.

FIGS. 2A-2D illustrate embodiments for a variety of configurations for the cover 208. The embodiments illustrated in FIGS. 2A-2D are segment views (i.e., partial views) used to provide a non-limiting illustration of different configurations of the matrix 222 and the flexible support members 224 used in the cover 208. For 30 example, FIG. 2A illustrates an embodiment in which the matrix 122 includes a first layer 201 and a second layer 203 of material positioned around the flexible support members 224. As illustrated in FIG. 2A, the flexible support members 224 have a knit configuration.

Figure 2B:
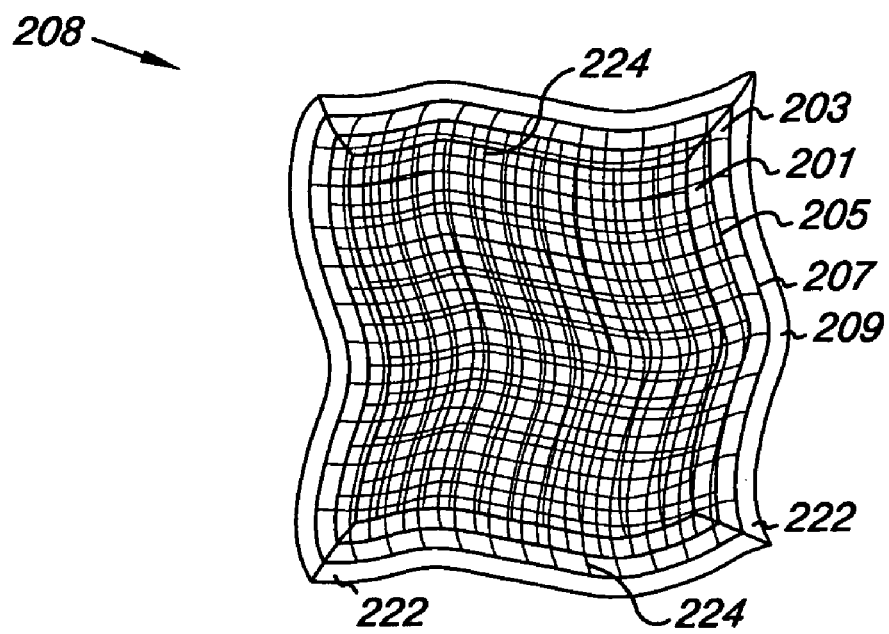

In an additional embodiment, FIG. 2B illustrates an embodiment in which the matrix 222 includes the first layer 201 and the second layer 203 of material positioned around a first course 205 of the flexible support members 224. The embodiment illustrated in FIG. 2B further includes a second course 207 of the flexible support members 224 positioned between the second layer 203 and a third layer 209 of the matrix 222. As illustrated, the first course 205 and the second course 207 of the flexible support members 224 in FIG. 2b have a woven configuration. As will be appreciated, different configurations of the flexible support members 224 (e.g., one flexible support member course having a knit configuration and one flexible support member course having a coil configuration) could be combined in the cover 204.

Figure 2C:
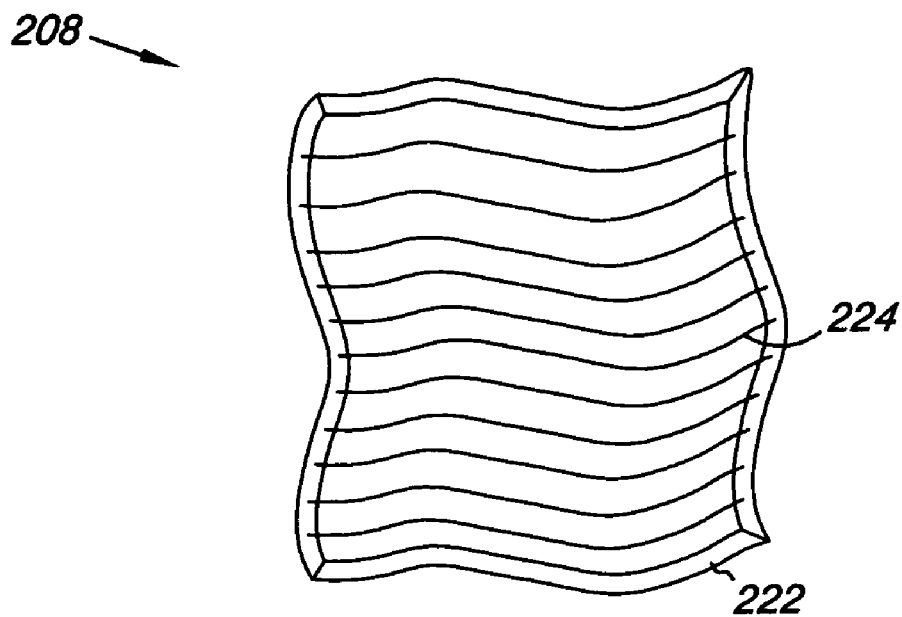

FIG. 2C illustrates another embodiment of the cover 208 that includes the matrix 222 surrounding the flexible support members 224 in a continuous helically wound coil configuration. As will be appreciated, the layers of the matrix 122 material can have all, some or none of the layers of the same or chemical composition. Similarly, the flexible support members 224 can have same or different configuration and/or chemical composition. In addition, mechanical properties of the cover 208 can be altered by changing the density, form, and/or texture of the flexible support members 224.

Figure 2D:
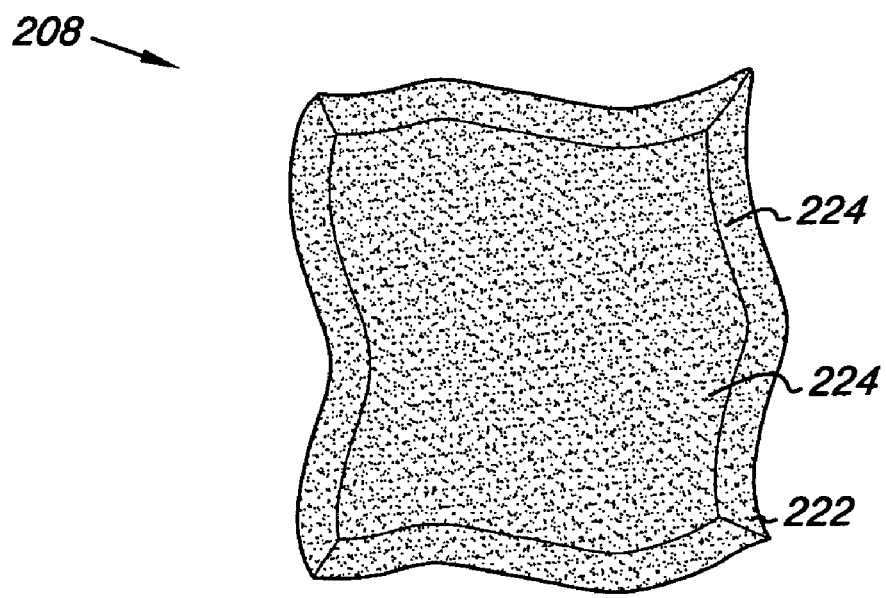

FIG. 2D illustrates another embodiment of the cover 208 that includes the matrix 222 that includes a distribution of the flexible support members 224. In one embodiment, the distribution of the flexible support members 224 can include a distribution of the nanostructures (e.g., basalt, and/or carbon nanotubules), as discussed herein. As will be appreciated, the layers of the matrix 122 material can have all, some or none of the layers of the same or chemical composition. Similarly, the flexible support members 224 can have same or different configuration and/or chemical composition. In addition, mechanical properties of the cover 208 can be altered by changing the density, form, and/or texture of the flexible support members 224.

Referring again to FIGS. 1A-1D, the fibers used in the flexible support members 124 may be made using a variety of processes that provide fibers with the desired properties (such as modulus, tensile strength, elongation etc.). Those skilled in the art of fiber processing are well versed in the art of extrusion, paste extrusion and stretching, solution spinning, electrostatic spinning, along with other fiber processing techniques, which may be used to provide polymer based fibers. These fibers may be oriented or drawn using conventional process to provide the desired degree of modulus, strength, and elongation. Generally, a fiber orientation process is used to improve the properties of the reinforcing fibers. The fibers can be oriented using a variety of drawing technologies such as single, multiple or continuous drawing steps with or without heating zones and/or relaxation. Additionally, these fibers may be post treated with various annealing, scouring, coating or surface treatment steps.

As will be appreciated, the cover 108 can be formed in any number of ways. For example, the embodiments of the cover 108 can be made by injecting, pouring, casting, or otherwise placing the matrix 122 material (e.g., a polymer solution) into a mold set-up comprised of a mold and the flexible support members 124. Alternatively, the embodiments of the cover 108 can be made by blending, or mixing, the matrix 122 material (e.g., a polymer) with flexible support members 124 (e.g., the carbon nano-tubules, or fibrous Basalt) before or during the injecting, pouring, or casting process into the mold.

The general processing steps include the selection of the materials from which the matrix 122 and the flexible support members 124 are made. In one embodiment, the cover 108 can generally be formed by use of compression molding in the mold set-up under a dry inert environment (for example, under nitrogen and/or argon) or under vacuum, at high enough temperatures, pressures, and long enough residence times (with proper cooling) to consolidate the composite. Alternately, the cover 108 composite can be formed by use of an autoclave, under a dry inert environment or under vacuum, at high enough temperatures and long enough residence times to consolidate the composite. Proper consolidation condition should provide a composite with no voids therein.

The flexible support members 124 are generally ceramic and/or polymeric (e.g., semi-crystalline polymers) while the matrix 122 materials are generally either amorphous or semi-crystalline polymers. In conventional composites, such as glass or carbon reinforced composites, the flexible support members 124 are not affected by consolidation temperature of the matrix 122. In addition, some or all of the fibers of the flexible support members 124 can be restrained during the consolidation process. The flexible support members 124 can be restrained during the heat treatment or the consolidation in a variety of ways, including, but not limited to, mechanical clamps or rack systems. This allows a reduction or a minimization in relaxation of fiber orientation. Additionally restraining the flexible support members 124 will control or avoid shrinkage of the flexible support members 124 during heat treatment and/or consolidation.

In an alternative embodiment, the matrix 122 material can be extruded or formed into a tubing of appropriate size and thickness. The material of the matrix 122 can then be cross-linked to raise the melt temperature of the resulting tube. The tube can then inflated and stretched to give the included polymer a specific molecular orientation. The tube of the matrix 122 material can then be placed over the combination of an inner layer of the matrix 122 material and the flexible support members 124 and the material of the matrix 122 heat-shrunk around the flexible support members 124. Alternatively, the flexible support members 124 can be dipped into molten material of the matrix 122 to form the cover 108. In yet another embodiment, suitable adhesive for the selected materials can be used to bond the matrix 122 material to additional layers of the matrix 122 material and to layers of the flexible support members 124. In an additional embodiment, the matrix 122 can be co-processed with the flexible support members 124 (e.g., nanostructures or fibrous basalt) so as to distribute the flexible support members 124 through the matrix 122.

In addition to the cover 108, the frame 102 too can be formed from a wide variety of materials and in a wide variety of configurations. Generally, frame 102 can have a unitary structure with an open frame configuration. For example, the open frame configuration can include frame members 126 that define openings 128 across the frame 102 through which valve leaflets 104 and 106 formed by the cover 108 can radially-collapse and radially-expand, as will be described herein.

In addition, the first end 112 and the second end 114 each include a plurality of end portions 130 that lay on a common plane. The plurality of end portions 130, however, need not all lay on the common plane. In other words, it is possible that one or more of the end portions 130 of the frame 102 lay above and/or below the common plane.

While the frames illustrated herein, for example frame 102, are shown as having a circular configuration, other configurations are also possible. For example, the frame 102 could have an elliptical configuration. As such, the present invention should not be limited to the illustration of the frames, such as frame 102, provided herein.

As illustrated in FIGS. 1A-1D, the frame 102 can further include a first leaflet connection region 132 and a second leaflet connection region 134 adjacent the second end 114 of the frame 102. In the present example, the cover 108 can be coupled, as described more fully herein, to at least the first leaflet connection region 132 and the second leaflet connection region 134. The cover 108 so coupled can then move (e.g., pivot) relative the first leaflet connection region 132 and the second leaflet connection region 134 between an open valve configuration (illustrated in FIGS. 1A and 1C) and a closed valve configuration (illustrated in FIGS. 1B and 1D). As illustrated in the closed valve configuration (FIGS. 1B and 1D), the open frame configuration of frame 102 allows cover 108 to move through the openings 128 in creating the reversible sealable opening 120 of the valve 100.

As illustrated in FIGS. 1A-1D, the first leaflet connection region 132 and the second leaflet connection region 134 can be positioned opposite each other along a common axis. In addition, the first leaflet connection region 132 and the second leaflet connection region 134 can be radially symmetric around a longitudinal central axis 138 of the frame 102. As illustrated, the first leaflet connection region 132 and the second leaflet connection region 134 can be positioned approximately one hundred eighty (180) degrees relative each other around the longitudinal central axis 138 of the frame 102. As will be appreciated, the first leaflet connection region 132 and the second leaflet connection region 134 need not necessarily display an equally spaced symmetrical relationship as described above in order to practice the embodiments of the present invention. For example, the radial relationship can have the first leaflet connection region 132 and the second leaflet connection region 134 positioned at values greater than one hundred eighty (180) degrees and less than one hundred eighty (180) degrees relative each other around the longitudinal central axis 138 of the frame 102.

The frame 102 can have similar and/or different cross-sectional geometries along its length. The similarity and/or the differences in the cross-sectional geometries can be based on one or more desired functions to be elicited from each portion of the frame 102. For example, the frame 102 can have a similar cross-sectional geometry along its length. Examples of cross-sectional geometries include, but are not limited to, round (e.g., circular, oval, and/or elliptical), rectangular geometries having perpendicular sides, one or more convex sides, or one or more concave sides; semi-circular; triangular; tubular; I-shaped; T-shaped; and trapezoidal. These embodiments, however, are not limited to the present examples as other cross-sectional geometries are also possible. As such, the present invention should not be limited to the frames provided in the illustration herein.

The valve 100 can further include a radial support member 140. The radial support member 140 can include a number of different configurations, as will be described herein. For example, in the embodiment illustrated in FIGS. 1A-1D, the radial support member 140 couples the first leaflet connection region 132 and the second leaflet connection region 134. In addition to coupling the connection regions 132 and 134, the radial support member 140 can also serve to stabilize the relative positions of the connection regions 132 and 134 (e.g., limit relative fluctuations of the connection regions 132 and 134).

In the present embodiment, the radial support member 140 can be in the form of a tubular ring 142 that joins to the first leaflet connection region 132 and the second leaflet connection region 134. The valve 100 can further include a second tubular ring 144 located at the first end 112 of the frame 102. The tubular rings 142 and 144 can also move radially as the valve 100 radially collapses and expands. As will be appreciated, the valve 100 could further include additional tubular rings located at one or more positions along the frame 102. In an alternative embodiment, the radial support member can be provided to the frame 102 of the valve 100 due in part to dimensional relationships imparted to the frame 102 that are more fully described in co-pending U.S. patent application Ser. No. 11/150,331 to Hill et al. entitled "Venous Valve Frame, System, and Method", which is hereby incorporated by reference in its entirety.

As illustrated, the cover 108 can be positioned over one or both of the radial support member 140 and the second tubular ring 144. As will be appreciated, the cover 108 need not extend to cover one or both of the radial support member 140 and the second tubular ring 144.

The compressible nature of the valve 100 can accommodate changes in body lumen size (e.g., diameter of the body lumen) by flexing to expand and/or contract to change the diameter of the frame 102. In one embodiment, the corner portions of the tubular rings 142 and 144, and the first leaflet connection region 132 and the second leaflet connection region 134 can act as springs to allow the valve 100 to resiliently radially collapse and expand. The frame 102 can also provide sufficient contact and expansion force with the surface of a body lumen wall to encourage fixation of the valve 100 and to prevent retrograde flow within the body lumen around the edges of the frame 102 and the surface of a lumen when combined with a closed state of the valve leaflets (described in more detail below) attached thereto. Anchoring elements (e.g., barbs) can also be included with valve 100, as will be discussed herein.

FIGS. 3A and 3B provide an example of the valve 300 in a collapsed state (FIG. 3A) and in an expanded state (FIG. 3B). As shown in FIGS. 3A and 3B, the valve 300 can travel between the collapsed and the expanded state along a radial travel path 346 (as shown in FIG. 3B), where there can be a change in a cross sectional area 348 of lumen 310. For example, the frame 302 can travel along the radial travel path 346 so as to change a width 350 of lumen 310. This can allow the valve 300 to react appropriately to the distension and contraction of a body lumen in which the valve 300 is placed. FIGS. 3A and 3B also provide an illustration of the valve 300 having a different configuration for the radial support members.

The embodiments of the frame discussed herein can also be constructed of one or more of a number of materials and in a variety of configurations. Generally, the frame embodiments can have a unitary structure with an open frame configuration. The frame can also be self-expanding. Examples of self-expanding frames include those formed from temperature-sensitive memory alloy (e.g., Nitinol) which changes shape at a designated temperature or temperature range. Alternatively, the self-expanding frames can include those having a spring-bias. In addition, the frame 102 can have a configuration that allows the frame embodiments be radially expandable through the use of a balloon catheter.

The embodiments of the frame, such as frame 102 in FIG. 1, can also be formed from one or more contiguous frame members. For example, the frame member of frame embodiments can be a single contiguous member. The single contiguous member can be bent around an elongate tubular mandrel to form the frame. The free ends of the single contiguous member can then be welded, fused, crimped, or otherwise joined together to form the frame. In an additional embodiment, the frame member of frame can be derived (e.g., laser cut, water cut) from a single tubular segment. In an alternative embodiment, methods of joining the frame member to create the elastic region include, but are not limited to, welding, gluing, and fusing the frame member. The frame can be heat set by a method as is typically known for the material which forms the frame.

The frame embodiments can be formed from a number of materials. For example, the frame can be formed from a biocompatible metal, metal alloy, polymeric material, or combination thereof. As discussed herein, the frame can be self-expanding or balloon expandable. In addition, the frame can be configured so as to have the ability to move radially between the collapsed state and the expanded state. To accomplish this, the material used to form the frame should exhibit a low elastic modulus and a high yield stress for large elastic strains that can recover from elastic deformations. Examples of suitable materials include, but are not limited to, medical grade stainless steel (e.g., 316 L), titanium, tantalum, platinum alloys, niobium alloys, cobalt alloys, alginate, or combinations thereof. Additional frame embodiments may be formed from a shape-memory material, such as shape memory plastics, polymers, and thermoplastic materials which are inert in the body. Shaped memory alloys having superelastic properties generally made from ratios of nickel and titanium, commonly known as Nitinol, are also possible materials. Other materials are also possible.

The lumen 110 can include a number of sizes. For example, the size of the lumen can be determined based upon the type of body lumen and the body lumen size in which the valve is to be placed. In an additional example, there can also be a minimum value for the width for the frame that ensures that the frame will have an appropriate expansion force against the inner wall of the body lumen in which the valve is being placed. For example, the diameter can range from 4 mm to 20 mm. Other diameter values are also possible.

In one embodiment, the frame can further include one or more anchoring elements. For example, the one or more anchoring elements can include, but are not limited to, one or more barbs 152 projecting from the frame 102. The valve can further include one or more radiopaque markers (e.g., tabs, sleeves, welds). For example, one or more portions of the frame can be formed from a radiopaque material. Radiopaque markers can be attached to and/or coated onto one or more locations along the frame. Examples of radiopaque material include, but are not limited to, gold, tantalum, and platinum. The position of the one or more radiopaque markers can be selected so as to provide information on the position, location and orientation of the valve during its implantation.

As discussed herein, valve 100 further includes cover 108 having surfaces defining the reversibly sealable opening 120 for unidirectional flow of a liquid through the lumen 110. For the embodiment illustrated in FIGS. 1A-1D, the cover 108 extends over at least a portion of the frame 102 to the first leaflet connection region 132 and the second leaflet connection region 134. The cover 108 extends between the first leaflet connection region 132 and the second leaflet connection region 134 to provide the first valve leaflet 104 and the second valve leaflet 106 of the valve leaflets. The first valve leaflet 104 and the second valve leaflet 106 include surfaces defining the reversibly sealable opening 120 extending between the first leaflet connection region 132 and the second, leaflet connection region 134 for unidirectional flow of a liquid through the valve 100.

As illustrated, the valve leaflets 104 and 106 include a region 154 of the cover 108 that can move relative the frame 102. The region 154 of the cover 108 can be unbound (i.e., unsupported) by the frame 102 and extends between the first leaflet connection region 132 and the second leaflet connection region 134 of the valve 100. This configuration permits the reversibly sealable opening 120 to open and close in response to the fluid pressure differential across the valve leaflets 104 and 106.

Figure 1B:
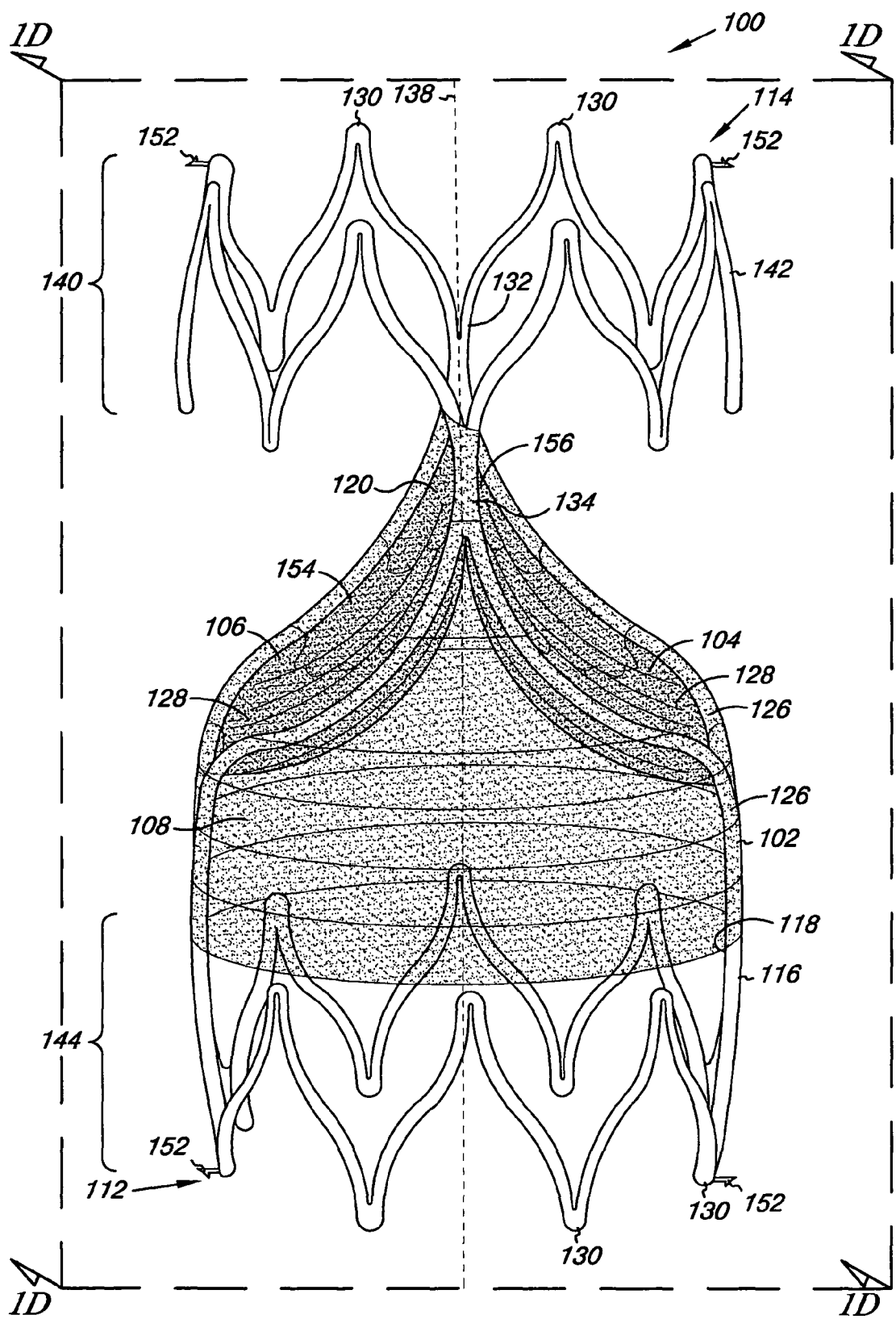
Figure 1C:
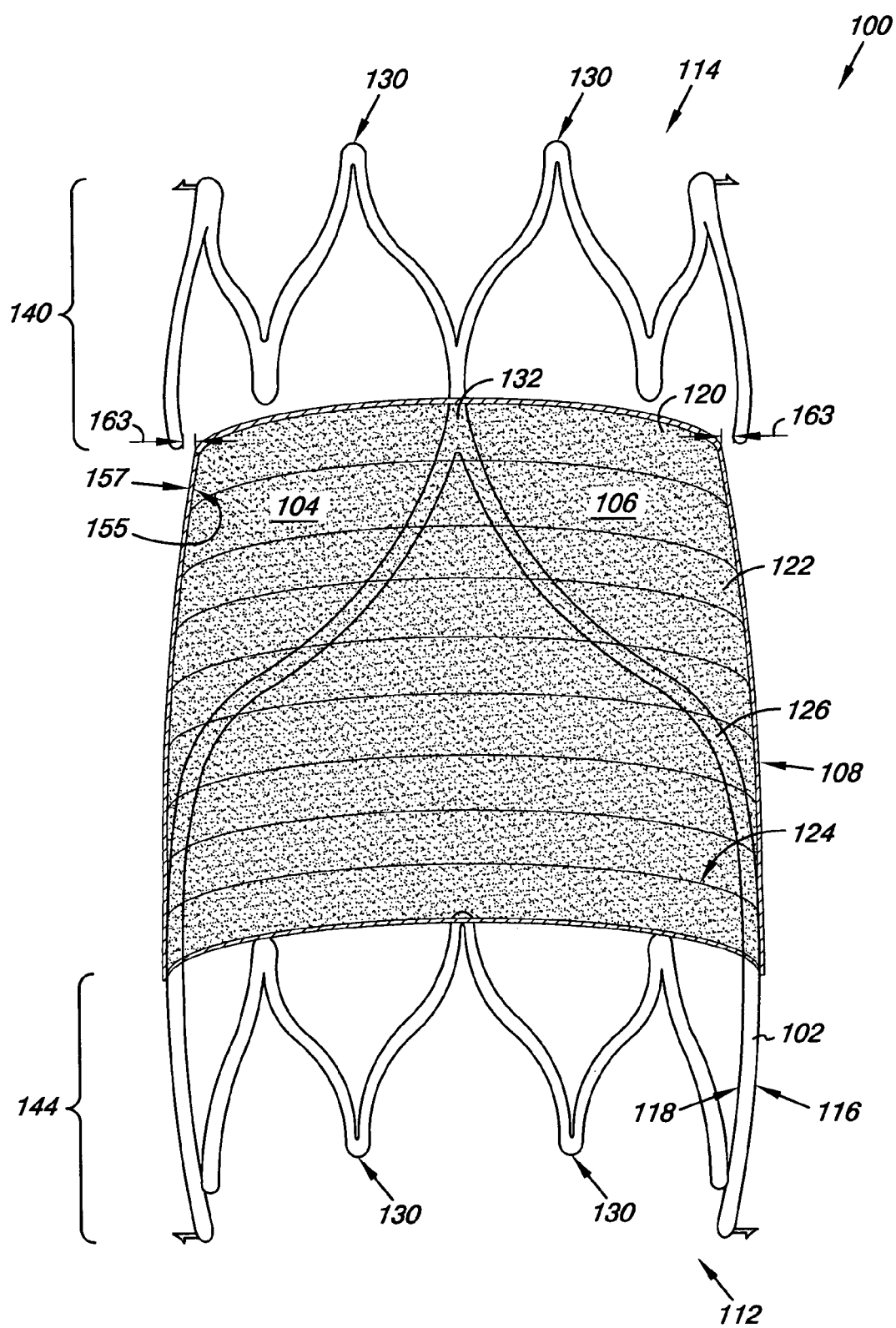
FIG. 1C illustrates a cross-sectional view of the valve illustrated in FIG. 1A taken along plane 1C-1C.

For example, under antegrade fluid flow (i.e., positive fluid pressure) from the first end 112 towards the second end 114 of the valve 100, the valve leaflets 104 and 106 can expand toward the inner surface 118 of the frame 102 to create an opening through which fluid is permitted to move. In one example, the valve leaflets 104 and 106 each expand to define a semi-tubular structure when fluid opens the reversibly sealable opening 120. An example of the open configuration for the valve is shown in FIGS. 1A and 1C.

Figure 1D:
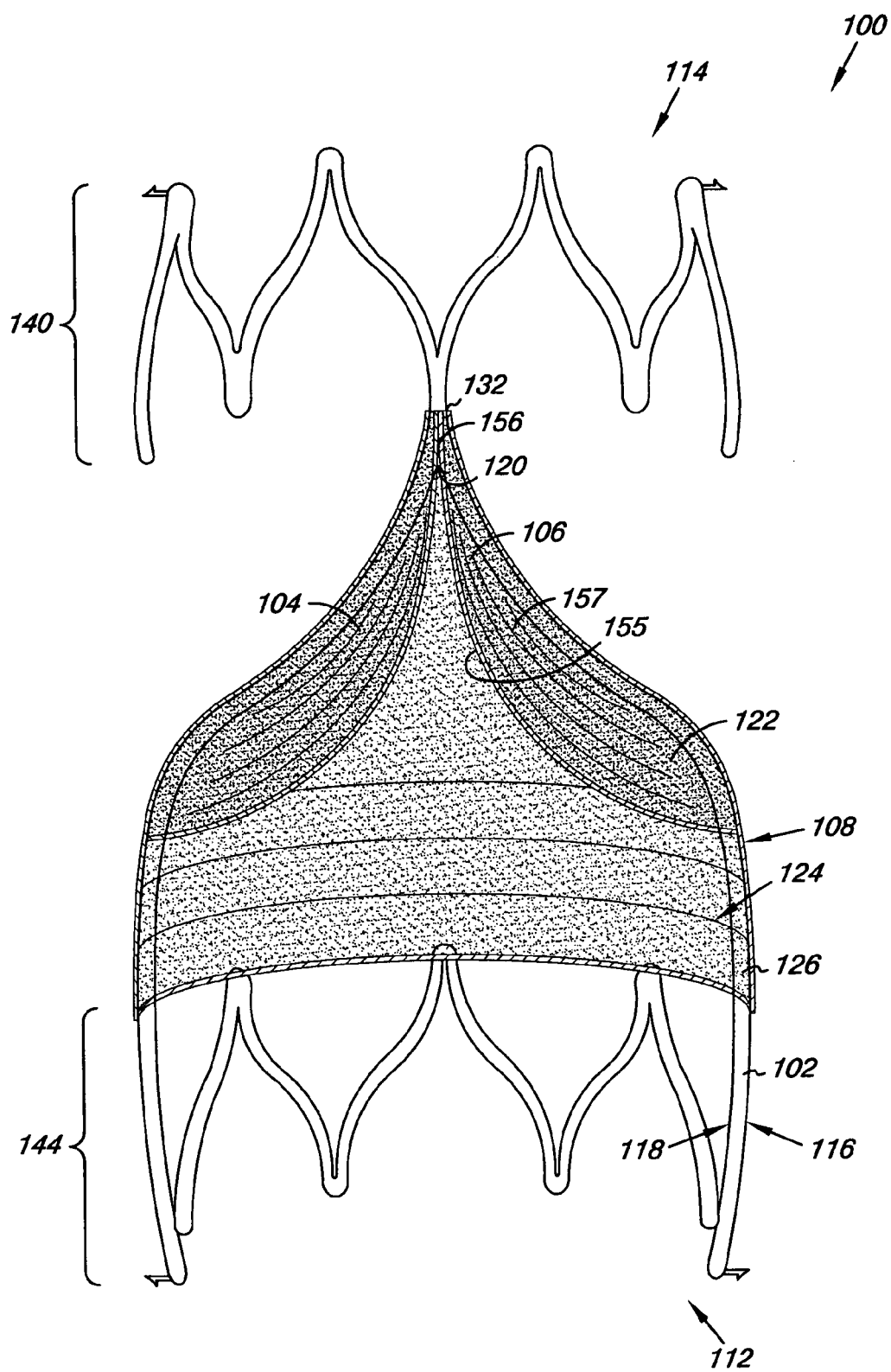
FIG. 1D illustrates a cross-sectional view of the valve illustrated in FIG. 1B taken along plane 1D-1D.

Under a retrograde fluid flow from the second end 114 towards the first end 112, the valve leaflets can move relative the inner surface 118 as the valve leaflets begin to close. In one example, a pocket exists between the frame 102 and each of the valve leaflets. The pocket allows fluid from the retrograde flow to develop a lower pressure on a first major face 155 of the valve leaflets than on the second major face 157 of the valve leaflets causing the valve leaflets to begin to close. As fluid pressure develops on the pocket regions formed on the second major face 157, the valve leaflets collapse, closing the reversibly sealable opening 120, thereby restricting retrograde fluid flow through the valve 100. In the closed configuration, the valve leaflets can each have a concave structure when fluid closes the reversibly sealable opening 120. In one embodiment, the concave structure can be imparted to the valve leaflets due to the configuration of the flexible support members 124 and/or the matrix 122. An example of the closed configuration for the valve is shown in FIGS. 1B and 1D.

Valve 100 provides an embodiment in which the surfaces defining the reversibly sealable opening 120 provide a bileaflet configuration (i.e., a bicuspid valve) for valve 100. Although the embodiments in FIGS. 1A-1D illustrate and describe a bi-leaflet configuration for the valve of the present invention, designs employing a different number of valve leaflets (e.g., tri-leaflet valve) are possible. For example; additional connection points (e.g., three or more) could be used to provide additional valve leaflets (e.g., a tri-leaflet valve).

The valve leaflets can have a variety of sizes and shapes. For example, each of the valve leaflets can have a similar size and shape. Alternatively, each of the valve leaflets need not have a similar size and shape (i.e., the valve leaflets can have a different size and shape with respect to each other). In addition, each of the valve leaflets include sufficient excess material spanning frame 102 such that fluid pressure (e.g., antegrade flow) acting on the region 154 of the valve leaflets forces the valve 100 into an open configuration (FIGS. 1A and 1C). The valve leaflets further include arcuate edges 156 that are positioned adjacent each other along a substantially catenary curve between the leaflet connection regions 132 and 134 in the closed configuration (FIGS. 1B and 1D) of valve 100. Similarly, arcuate edges 156 can define opening 120 when the valve 100 is in the open configuration (FIGS. 1A and 1C).

In an additional embodiment, in the open configuration the portion of the cover 108 forming the valve leaflets 104 and 106 provides sufficient excess material spanning between the leaflet connection regions 132 and 134 to allow the leaflets to take on a semi-tubular structure, as shown in FIG. 1A, when fluid pressure opens the valve 100. In an additional embodiment, arcuate edges 156 of valve 100 can open to approximately the full inner diameter of a body lumen. Alternatively, the arcuate edges 156 of valve 100 can open to approximately a diameter that is less than the full inner of a body lumen. FIGS. 1A and 1C provide an illustration of this latter embodiment, where a space 163 can be present between the second major face 157 of the valve leaflets and the inner surface 118 of the frame 102.

Each of the regions 154 of the valve leaflets can further include a concave structure that allows the valve leaflets to better collect retrograde fluid flow to urge the valve leaflets towards the closed configuration. For example, as retrograde flow begins, the valve leaflets respond by moving towards the center of valve 100. As the valve leaflets approach the center of the leaflets make sufficient contact to effectively close valve 100 and restrict retrograde fluid flow.

As discussed herein, the cover 108 can be located over at least the outer surface 116 and the inner surface 118 of the frame 102 to form the valve leaflets 104 and 106 as described herein. Alternatively, the cover 108 can be located over the inner surface 118 of the frame 102, or the cover 108 can be located over the outer surface 116 of the frame 102 to form the valve leaflets 104 and 106 as described herein. Numerous techniques may be employed to laminate or bond cover 108 on the outer surface 116 and/or the inner surface 118 of the frame 102, including heat setting, adhesive welding, application of uniform force and other bonding techniques. Additionally, the cover 108 may be folded over the first end 112 of the frame 102 to provide the cover 108 on both the outer surface 116 and the inner surface 118. Cover 108 can also be joined to itself and/or the members 126 according to the methods described in U. S. Patent Application Publication US 2002/0178570 to Sogard et al., which is hereby incorporated by reference in its entirety.

The cover 108 can also be coupled to the connection regions so as to form the valve leaflets, as discussed herein. In one embodiment, the cover 108 can be in the form of a sheet or a sleeve of material, as discussed herein, which can be connected to the frame 102. Other forms, including intermediate forms, of the cover 108 are also possible.

The cover 108 can be coupled to the frame 102, including the connection regions 132 and 134, in a variety of ways so as to provide the various embodiments of the valve of the present invention. For example, a variety of fasteners can be used to couple the cover 108 to the frame 102 so as to form the valve 100. Suitable fasteners can include, but are not limited to, biocompatible staples, glues, sutures or combinations thereof. In an additional embodiment, the cover 108 can be coupled to the frame 102 through the use of heat sealing, solvent bonding, adhesive bonding, or welding cover 108 to either a portion of the cover 108 (i.e., itself) and/or the frame 102.

The cover 108, including the valve leaflets 104 and 106, may also be treated and/or coated with any number of surface or material treatments. For example, suitable bioactive agents which may be incorporated with or utilized together with embodiments of the present invention may include silver antimicrobial agents, metallic antimicrobial materials, growth factors, cellular migration agents, cellular proliferation agents, anti-coagulant substances, stenosis inhibitors, thrombo-resistant agents, antibiotic agents, anti-tumor agents, anti-proliferative agents, growth hormones, antiviral agents, anti- angiogenic agents, angiogenic agents, cholesterol-lowering agents, vasodilating agents, agents that interfere with endogenous vasoactive mechanisms, hormones, their homologs, derivatives, fragments, pharmaceutical salts and combinations thereof.

In the various embodiments of the present invention, the most useful bioactive agents can include those that modulate thrombosis, those that encourage cellular ingrowth, throughgrowth, and endothelialization, those that resist infection, and those that reduce calcification. For example, the cover 108 can be treated with one or more biologically active compounds and/or materials that may promote and/or inhibit endothelial, smooth muscle, fibroblast, and/or other cellular growth onto or into the cover 108, including the valve leaflets. Similarly, the cover 108 may be seeded and covered with cultured tissue cells (e.g., endothelial cells) derived from a either a donor or the host patient which are attached to the valve leaflets. The cultured tissue cells may be initially positioned to extend either partially or fully over the valve leaflets.

Cover 108, in addition to forming valve leaflets 104 and 106, can also be capable of inhibiting thrombus formation, as discussed herein. Additionally, cover 108 may either prevent or facilitate tissue ingrowth therethrough, as the particular application for the valve 100 may dictate. For example, cover 108 on the outer surface 116 may be formed from a porous material to facilitate tissue ingrowth therethrough, while cover 108 on the inner surface 118 may be formed from a material or a treated material which inhibits tissue ingrowth.

Cells can be associated with the present invention. For example, cells that have been genetically engineered to deliver bioactive proteins, such as the above mentioned growth factors or antibodies, to the implant site can be associated with the present invention. Cells can be of human origin (autologous or allogenic) or from an animal source (xenogenic). Cells can be pre-treated with medication or pre-processed such as by sorting or encapsulation. The delivery media can be formulated as needed to maintain cell function and viability.

Thrombo-resistant agents associated with the present invention can include, but are not limited to, the following: heparin, heparin sulfate, hirudin, hyaluronic acid, chondroitin sulfate, dermatin sulfate, keratin sulfate, PPack (detropyenylalanine praline arginine chloromethylketone), lytic agents, including urokinase and streptokinase, their homologs, analogs, fragments, derivatives and pharmaceutical salts thereof.

Anti-coagulants can include, but are not limited to, the following: D-Phe-Pro-Arg chloromethyl ketone, an RGD peptide-containing compound, heparain, antithrombin compounds, platelet receptor antagonists, anti-thrombin antibodies, anti-platelet receptor antibodies, aspirin, prostaglandin inhibitors, platelet inhibitors, tick antiplatelet peptides and combinations thereof.

Antibiotic agents can include, but are not limited to, the following agents,: penicillins, cephalosportins, vancomycins, aminoglycosides, quinolonges, polymyxins, erythromycins, tetracyclines, chloraphenicols, clindamycins, lincomycins, sulfonamides, their homologs, analogs, derivatives, pharmaceutical salts and combinations thereof.

Anti-proliferative agents for use in the present invention can include, but are not limited to, the following: paclitaxel, sirolimus, everolimus, or monoclonal antibodies capable of blocking smooth muscle cell proliferation, related compounds, derivatives, and combinations thereof.

Vascular cell growth inhibitors can include, but are not limited to, the following: growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of a an antibody and a cytotoxin.

Vascular cell growth promoters can include, but are not limited to, transcriptional activators and transcriptional promoters. And, anti-inflammatory agents can include, but are not limited to, the following: dexametbasone, prednisolone, corticosterone, budesonide, estrogen, sulfasalazinemesalamne, and combinations thereof.

Figure 4:
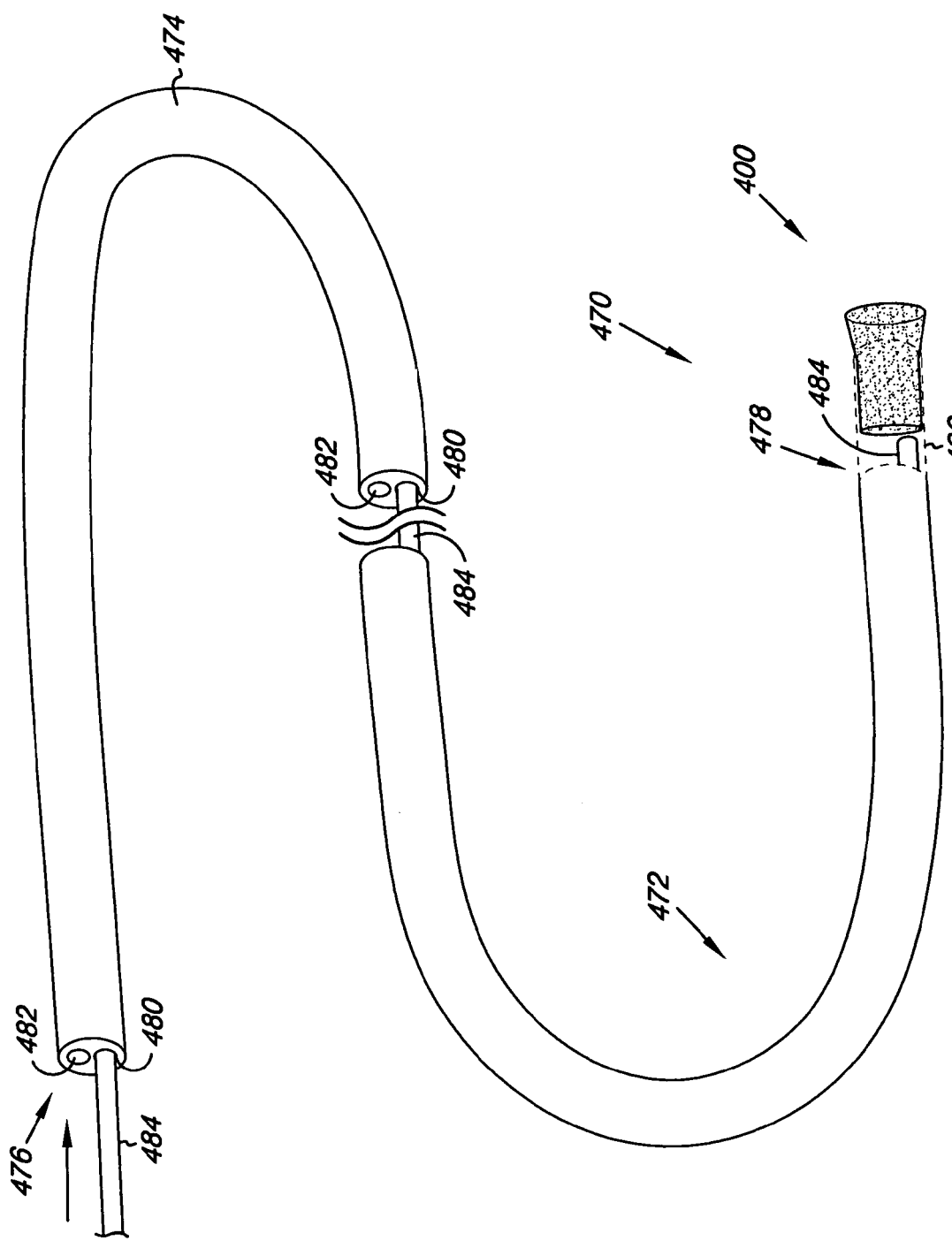
FIG. 4 illustrates an embodiment of a system that includes a valve.

FIG. 4 illustrates one embodiment of a system 470. System 470 includes valve 400, as described herein, reversibly joined to catheter 472. The catheter 472 includes an elongate body 474 having a proximal end 476 and a distal end 478, where valve 400 can be located between the proximal end 476 and distal end 478. The catheter 472 can further include a lumen 480 longitudinally extending to the distal end 478. In one embodiment, lumen 480 extends between proximal end 476 and distal end 478 of catheter 472. The catheter 472 can further include a guidewire lumen 482 that extends within the elongate body 474, where the guidewire lumen 482 can receive a guidewire for positioning the catheter 472 and the valve 400 within a body lumen (e.g., a vein of a patient).

The system 470 can further include a deployment shaft 484 positioned within lumen 480, and a sheath 486 positioned adjacent the distal end 478. In one embodiment, the valve 400 can be positioned at least partially within the sheath 486 and adjacent the deployment shaft 484. The deployment shaft 484 can be moved within the lumen 478 to deploy valve 400. For example, deployment shaft 484 can be used to push valve 400 from sheath 486 in deploying valve 400.

Figure 5:
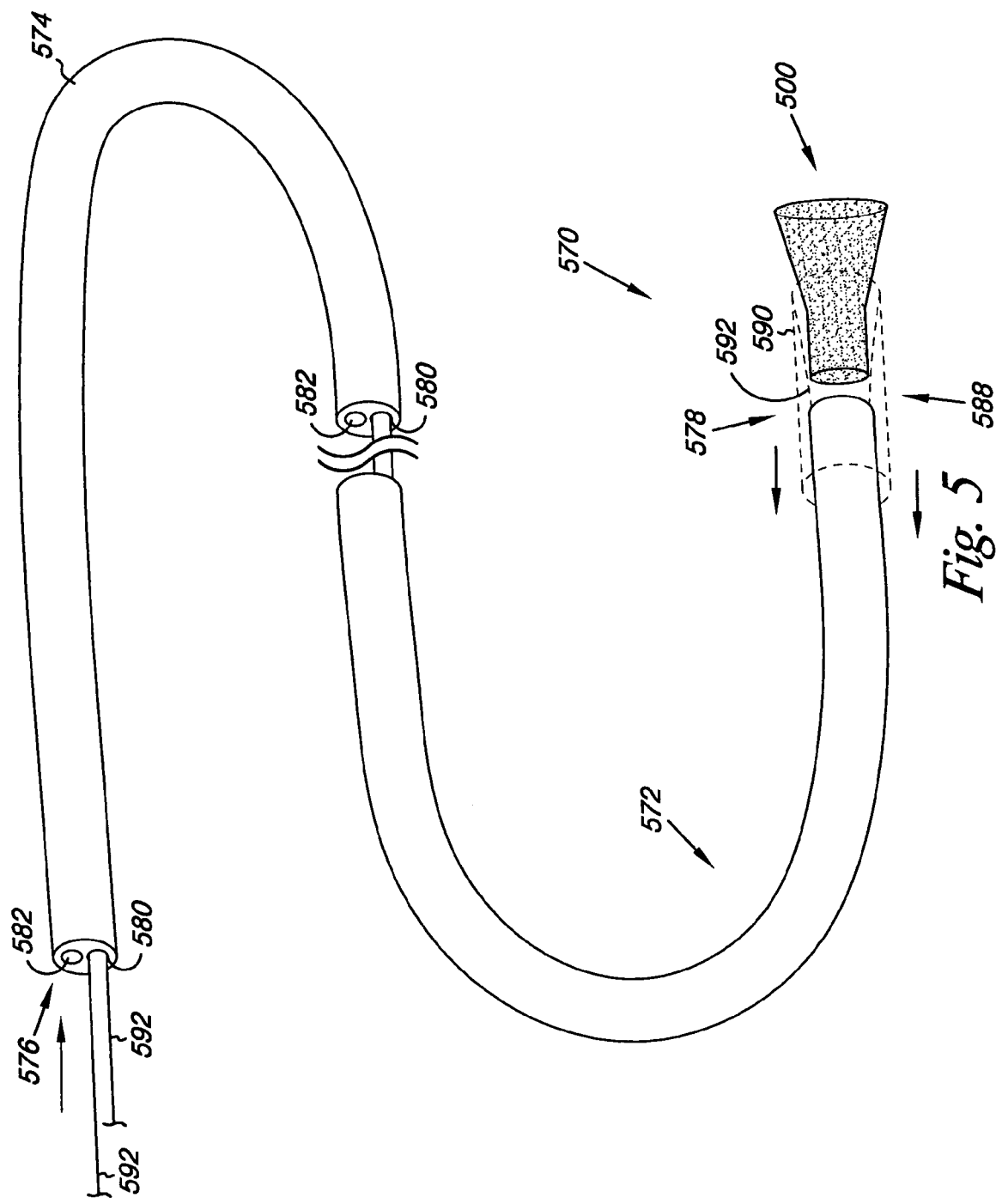
FIG. 5 illustrates an embodiment of a system that includes a valve.

FIG. 5 illustrates an additional embodiment of the system 570. The catheter 572 includes elongate body 574, lumen 580, a retraction system 588 and a retractable sheath 590. The retractable sheath 590 can be positioned over at least a portion of the elongate body 574, where the retractable sheath 590 can move longitudinally along the elongate body 574. The valve 500 can be positioned at least partially within the retractable sheath 590, where the retractable sheath 590 moves along the elongate body 574 to deploy the valve 500. In one embodiment, retraction system 588 includes one or more wires 592 coupled to the retractable sheath 590, where the wires are positioned at least partially within and extend through lumen 580 in the elongate body 574. Wires of the retraction system 588 can then be used to retract the retractable sheath 590 in deploying valve 500.

Figure 6:
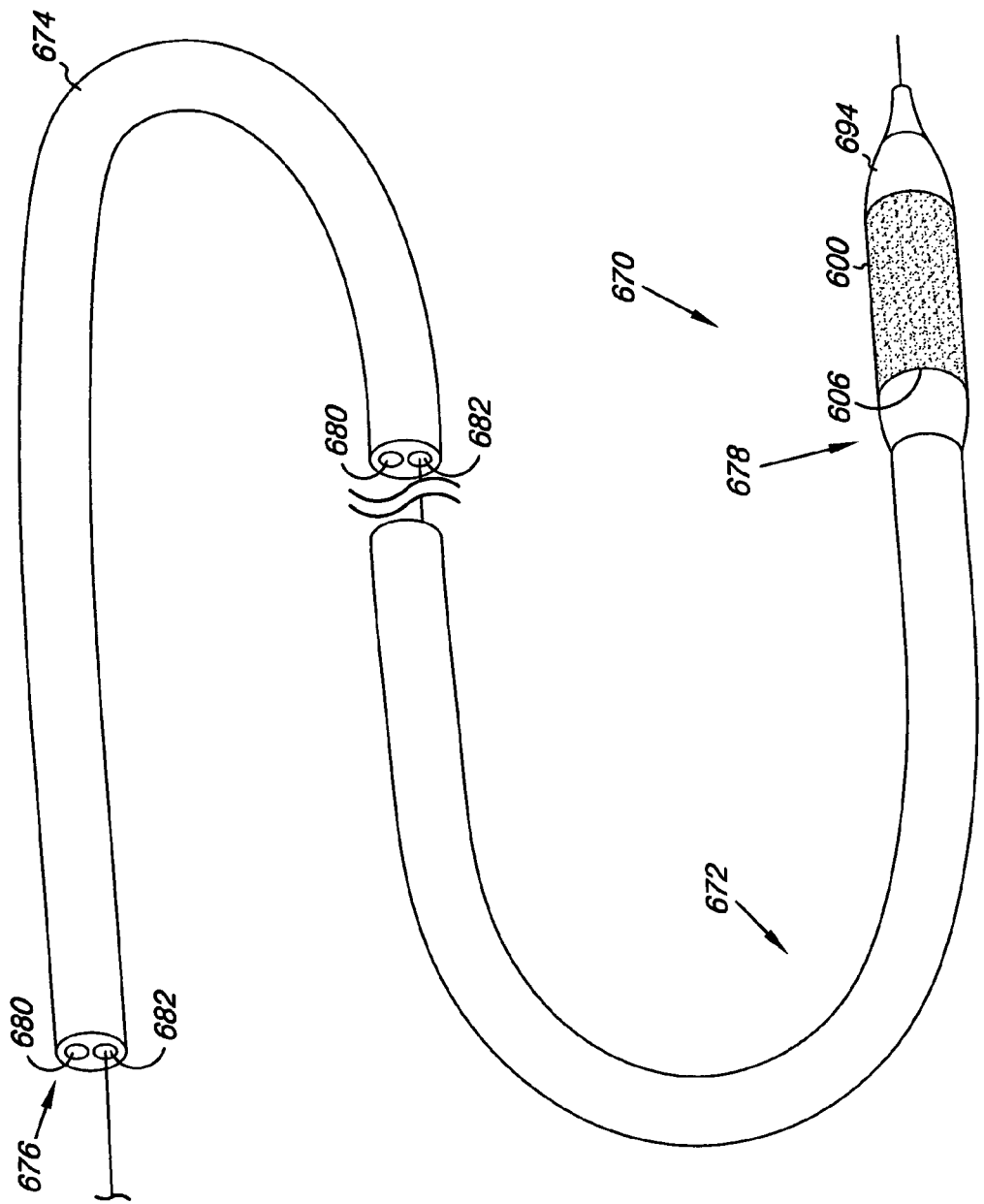
FIG. 6 illustrates an embodiment of a system that includes a valve.

FIG. 6 illustrates an additional embodiment of the system 670. The catheter 672 includes elongate body 674, an inflatable balloon 694 positioned adjacent the distal end 678, and a lumen 680 longitudinally extending in the elongate body 674 of the catheter 672 from the inflatable balloon 694 to the proximal end 676. In the present example, the inflatable balloon 694 can be at least partially positioned within the lumen 606 of the valve 600. The inflatable balloon 694 can be inflated through the lumen 680 to deploy the valve 600.

The embodiments of the present invention further include methods for forming the valve of the present invention, as discussed herein. For example, the method of forming the valve can include forming the frame having the leaflet connection regions, as described. The method can include providing the radial support member, or members, on the frame for the leaflet connection regions. As discussed herein, the radial support member can include the tubular rings adjacent the leaflet connection regions. The method also includes providing the cover on the frame, where connecting the cover to the leaflet connection regions provides at least the first leaflet and the second leaflet of the valve having surfaces defining the reversibly sealable opening for unidirectional flow of a liquid through the valve.

In an additional example, the valve can be reversibly joined to the catheter, which can include a process of altering the shape of the valve from a first shape, for example an expanded state, to the compressed state, as described herein. For example, the valve can be reversibly joined with the catheter by positioning valve in the compressed state at least partially within the sheath of the catheter. In one embodiment, positioning the valve at least partially within the sheath of the catheter includes positioning the valve in the compressed state adjacent the deployment shaft of the catheter. In an another embodiment, the sheath of the catheter functions as a retractable sheath, where the valve in the compressed state can be reversibly joined with the catheter by positioning the valve at least partially within the reversible sheath of the catheter. In a further embodiment, the catheter can include an inflatable balloon, where the balloon can be positioned at least partially within the lumen of the valve, for example, in its compressed state.

The embodiments of the valve described herein may be used to replace, supplement, or augment valve structures within one or more lumens of the body. For example, embodiments of the present invention may be used to replace an incompetent venous valve and help to decrease backflow of blood in the venous system of the legs.

In one embodiment, the method of replacing, supplementing, and/or augmenting a valve structure can include positioning at least part of the catheter including the valve at a predetermined location within the lumen of a body. For example, the predetermined location can include a position within a body lumen of a venous system of a patient, such as a vein of a leg.

In one embodiment, positioning the catheter that includes the valve within the body lumen of a venous system includes introducing the catheter into the venous system of the patient using minimally invasive percutaneous, transluminal catheter based delivery system, as is known in the art. For example, a guidewire can be positioned within a body lumen of a patient that includes the predetermined location. The catheter, including valve, as described herein, can be positioned over the guidewire and the catheter advanced so as to position the valve at or adjacent the predetermined location. In one embodiment, radiopaque markers on the catheter and/or the valve, as described herein, can be used to help locate and position the valve.

The valve can be deployed from the catheter at the predetermined location in a number of ways, as described herein. In one embodiment, valve of the present invention can be deployed and placed in a number of vascular locations. For example, valve can be deployed and placed within a major vein of a patient's leg. In one embodiment, major veins include, but are not limited to, those of the peripheral venous system. Examples of veins in the peripheral venous system include, but are not limited to, the superficial veins such as the short saphenous vein and the greater saphenous vein, and the veins of the deep venous system, such as the popliteal vein and the femoral vein.

As discussed herein, the valve can be deployed from the catheter in a number of ways. For example, the catheter can include the retractable sheath in which valve can be at least partially housed, as discussed herein. Valve can be deployed by retracting the retractable sheath of the catheter, where the valve self-expands to be positioned at the predetermined location. In an additional example, the catheter can include a deployment shaft and sheath in which valve can be at least partially housed adjacent the deployment shaft, as discussed herein. Valve can be deployed by moving the deployment shaft through the catheter to deploy valve from the sheath, where the valve self-expands to be positioned at the predetermined location. In an additional embodiment, the valve can be deployed through the use of an inflatable balloon.

Once implanted, the valve can provide sufficient contact and expansion force against the body lumen wall to prevent retrograde flow between the valve and the body lumen wall. For example, the valve can be selected to have a larger expansion diameter than the diameter of the inner wall of the body lumen. This can then allow valve to exert a force on the body lumen wall and accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

In addition, the use of both the radial support member and/or the support frame region of the valve can provide a self centering aspect to valve within a body lumen. In one embodiment, the self centering aspect resulting from the radial support member and/or the support frame region may allow valve to maintain a substantially coaxial alignment with the body lumen (e.g., such as a vein) as valve leaflets deflect between the open and closed configurations so as to better seal the reversible opening when valve is closed.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the frame 102 and/or the cover 108 can be coated with a nonthrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A valve, comprising:
a frame having an inner frame surface, an outer frame surface opposite the inner frame surface, a first leaflet connection a second leaflet connection region, a tubular radial support member that includes a first frame end and extends from the first leaflet connection region and the second leaflet connection region, a tubular ring that includes a second frame end, a first member, a second frame member, a third frame member, and a fourth frame member, where the frame members define openings across the frame and each of the frame members immediately extend from the tubular ring towards the tubular radial support member such that the first frame member merges with the second frame member to form the first leaflet connection region and the third frame member merges with the fourth frame member to form the second leaflet connection region, where the first leaflet connection region and the second leaflet connection region immediately extend from the tubular radial support member; and
a frame cover having integrated flexible support members, a frame cover interior, a frame cover exterior opposite the frame cover interior, a first frame cover terminus proximate to the first frame end, a second frame cover terminus proximate to the second frame end where the frame cover provides:
a first leaflet coupled to the first leaflet connection region and the second leaflet connection region;
a second leaflet coupled to the first leaflet connection region and the second leaflet connection region, where the first leaflet and the second leaflet have surfaces defining a reversibly sealable opening for unidirectional flow of a liquid through the valve and where the first valve leaflet and the second valve leaflet pass through the openings defined by the frame members to radially-expand and radially-collapse; and
an area defined by the frame cover exterior at the second frame cover terminus that is less than an area defined by the inner frame surface at the second frame end and less than an area defined by the frame cover at the first frame cover terminus so as to provide a space between the frame cover exterior at the second frame cover terminus and the inner frame surface of the radial support member when the frame cover is in an open position.

2. The valve of claim 1, wherein the first leaflet and the second leaflet are formed of a first material and the integrated flexible support members are formed of a second material.

3. The valve of claim 2, wherein the integrated flexible support members are laminated between at least two layers of the first material.

4. The valve of claim 3, wherein the first material of the first leaflet and the second leaflet includes a thermoplastic.

5. The valve of claim 1, wherein the first leaflet and the second leaflet include a predetermined shape and the flexible support members stabilize the predetermined shape in the first leaflet and the second leaflet.

6. The valve of claim 1, wherein the second material of the integrated flexible support members includes spun-fibers of a ceramic.

7. The valve of claim 6, wherein the ceramic includes basalt.

8. The valve of claim 1, wherein the integrated flexible support members are oriented to provide circumferential support to the first leaflet and the second leaflet.

9. The valve of claim 8, wherein the integrated flexible support members are in a configuration selected from the group consisting of woven, matted, coiled, rings, braided and knitted.

10. The valve of claim 1, wherein the first leaflet has a first leaflet first major face on the frame cover interior and a first leaflet second major face on the frame cover exterior and the second leaflet has a second leaflet first major face on the frame cover interior and a second leaflet second major face on the frame cover exterior, such that when the valve is in the open position:
a first space is present between the inner surface of the tubular radial support member and the first leaflet second major face, so that a line perpendicular to the longitudinal axis of the frame that passes through the first space and the first leaflet second major face passes through the frame cover at only two points; and
second space is present between the inner surface of the tubular radial support member and the second leaflet second major face, so that a line perpendicular to the longitudinal axis of the frame that passes through the second space and the second leaflet major face passes through the frame cover at only two points.

* * * * *